(12) United States Patent
Alimperti et al.

(10) Patent No.: US 11,684,699 B2
(45) Date of Patent: *Jun. 27, 2023

(54) THREE-DIMENSIONAL PRINTED HYDROXYAPATITE COMPOSITE SCAFFOLDS FOR BONE REGENERATION, PRECURSOR COMPOSITIONS AND METHODS OF PRINTING

(71) Applicant: ADA Science and Research Institute LLC, Chicago, IL (US)

(72) Inventors: Stella Alimperti, Germantown, MD (US); Yoontae Kim, Rockville, MD (US); Eun-Jin Lee, Rockville, MD (US); Laurence C Chow, Potomac, MD (US); Shozo Takagi, Gaithersburg, MD (US)

(73) Assignee: ADA Science and Research Institute LLC, Chicago, IL (US)

( * ) Notice: Subject to any disclaimer, the term of this patent is extended or adjusted under 35 U.S.C. 154(b) by 303 days.

This patent is subject to a terminal disclaimer.

(21) Appl. No.: 16/894,128

(22) Filed: Jun. 5, 2020

(65) Prior Publication Data
US 2021/0260249 A1   Aug. 26, 2021

Related U.S. Application Data

(60) Provisional application No. 62/981,070, filed on Feb. 25, 2020.

(51) Int. Cl.
*A61L 27/44* (2006.01)
*A61L 27/42* (2006.01)
*A61L 24/00* (2006.01)

(52) U.S. Cl.
CPC ......... *A61L 27/446* (2013.01); *A61L 24/0084* (2013.01); *A61L 27/427* (2013.01); *A61L 2430/02* (2013.01); *A61L 2430/38* (2013.01)

(58) Field of Classification Search
None
See application file for complete search history.

(56) References Cited

U.S. PATENT DOCUMENTS

| | | | |
|---|---|---|---|
| 1,058,425 | A | 4/1913 | Gierl |
| 6,730,252 | B1 | 5/2004 | Teoh |

(Continued)

FOREIGN PATENT DOCUMENTS

| | | | | |
|---|---|---|---|---|
| CN | 107982577 A | 5/2018 | | |
| WO | WO-2009105614 A2 * | 8/2009 | ............. | A61L 27/46 |

(Continued)

OTHER PUBLICATIONS

Abhijit Roy, Siddharth Jhunjhunwala, Emily Bayer, Morgan Fedorchak, Steve R. Little, Prashant N. Kumta. "Porous calcium phosphate-poly (lactic-co-glycolic) acid composite bone cement: A viable tunable drug delivery system." Materials Science and Engineering C, vol. 59 (2016), pp. 92-101. (Year: 2016).*

(Continued)

*Primary Examiner* — Isaac Shomer
(74) *Attorney, Agent, or Firm* — Saul Ewing LLP; Domingos J. Silva; Dennis Ostrovsky

(57) ABSTRACT

A three-dimensional, biocompatible scaffold precursor composition for room-temperature printing a bio-compatible polymer/hydroxyapatite composite scaffold includes a room-temperature slurry, comprising a mixture of a sold phase that includes a mixture of tetracalcium phosphate (TTCP; $Ca_4(PO_4)_2O$) and dicalcium phosphate anhydrous (DCPA; $CaHPO_4$), and a liquid phase that includes a polymer in a solvent. The solvent may be Ethanol (EtOH) or Tetrahydrofuran (THF), and the polymer may be polyvinyl butyral (PVB), polycaprolactone (PCL), or poly lactic-co-glycolic acid (PLGA). The slurry is printed at room temperature in aqueous phosphate ($NaH_2PO_4$) bath, which (Continued)

works as hardening accelerator, forming the polymer/hydroxyapatite composite scaffold.

7 Claims, 17 Drawing Sheets

(56) References Cited

U.S. PATENT DOCUMENTS

| | | | |
|---|---|---|---|
| 7,968,026 B1 | 6/2011 | Teoh | |
| 8,071,007 B1 | 12/2011 | Teoh | |
| 8,105,517 B2 | 1/2012 | Suzuki | |
| 8,702,808 B2 | 4/2014 | Teoh | |
| 8,829,073 B2 | 9/2014 | Nies | |
| 8,906,111 B2 | 12/2014 | Tei | |
| 9,849,211 B2 | 12/2017 | Nies | |
| 10,391,203 B2 | 8/2019 | Thurner | |
| 2006/0263443 A1* | 11/2006 | Chow | A61K 31/19 424/603 |
| 2007/0092580 A1* | 4/2007 | Chow | A61L 27/54 424/602 |
| 2007/0098652 A1* | 5/2007 | Chow | A61Q 11/00 424/52 |
| 2010/0069455 A1 | 3/2010 | Takato | |
| 2010/0262259 A1 | 10/2010 | Tei | |
| 2010/0269736 A1* | 10/2010 | Chow | A61L 24/001 106/690 |
| 2014/0271769 A1 | 9/2014 | Nies | |
| 2015/0066144 A1 | 3/2015 | Nies | |
| 2016/0354518 A1 | 12/2016 | Xu | |
| 2017/0265965 A1* | 9/2017 | Chow | A61K 6/851 |
| 2018/0243484 A1 | 8/2018 | Shah | |
| 2018/0296343 A1 | 10/2018 | Wei | |
| 2020/0001498 A1 | 1/2020 | Kuster | |

FOREIGN PATENT DOCUMENTS

| | | |
|---|---|---|
| WO | WO2013034180 A1 | 3/2013 |
| WO | WO2019211449 A1 | 11/2019 |

OTHER PUBLICATIONS

FC Driessens, MG Boltong, EAP De Maeyer, RMH Verbeeck. "Effect of temperature and immersion on the setting of some calcium phosphate cements." Journal of Materials Science: Materials in Medicine, vol. 11, 2000, pp. 453-457. (Year: 2000).*

F Yener, B Yalcinkaya. "Electrospinning of polyvinyl butyral in different solvents." e-Polymers, No. 021, 2013, pp. 1-14. (Year: 2013).*

Susan L. Ishaug, Genevieve M. Crane, Michael J. Miller, Alan W. Yasko, Michael J. Yaszemski, and Antonios G. Mikos. "Bone formation by three-dimensional stromal osteoblast culture in biodegradable polymer scaffolds." Journal of Biomedical Materials Research, vol. 36, 1997, pp. 17-28. (Year: 1997).*

Laurence C. Chow and Shozo Takagi. "A Natural Bone Cement—A Laboratory Novelty Led to the Development of Revolutionary New Biomaterials." Journal of Research of the National Institute of Standards and Technology, vol. 106, No. 6, Nov.-Dec. 2001, pp. 1029-1033. (Year: 2001).*

Shozo Takagi, Laurence C. Chow, Satoshi Hirayama, and Akiyoshi Sugawara. "Premixed Calcium-Phosphate Cement Pastes." Journal of Biomedical Materials Research Part B: Applied Biomaterials, vol. 67B, 2003, pp. 689-696. (Year: 2003).*

Kumar, Anuj; Additive Manufacturing Methods for Producing Hydroxyapatite and Hydroxyapatite-Based Composite Scaffolds: A Review; Frontiers in Materials; Dec. 17, 2019; pp. 1-20; vol. 6, Article 313; frontiersin.org; US.

Korn, Paula; 3D Printing of Bone Grafts for Cleft Alveolar Osteoplasty—In vivo Evaluation in a Preclinical Model; Frontiers in Bioengineering and Biotechnology; Mar. 25, 2020; pp. 1-16; vol. 8, Article 217; frontiersin.org; US.

Ahlfeld, Tilman; Toward Biofabrication of Resorbable Implants Consisting of a Calcium Phosphate Cement and Fibrin—A Characterization In Vitro and In Vivo; International Journal of Molecular Sciences; Jan. 26, 2021; pp. 1-16; 22:1218; MDPI, CH.

Richter, Richard Frank; Development and Characterization of Composites Consisting of Calcium Phosphate Cements and Mesoporous Bioactive Glass for Extrusion-Based Fabrication; Materials; Jun. 24, 2019; pp. 1-16; 12:2022; MDPI; CH.

O'Neill, R.; Critical review: Injectability of calcium phosphate pastes and cements; Acta Biomaterialia; Nov. 9, 2016; pp. 1-19; 50 (2017); Elsevier; GB.

Vella, Joseph B.; Three dimensional printed calcium phosphate and poly(caprolactone) composites with improved mechanical properties and preserved microstructure; Mar. 1, 2019; J. Biomed Mater Res. A.; pp. 663-672; 106 (3) PMC, US.

Heinemann, S.; Properties of injectable ready-to-use calcium phosphate cement based on water-immiscible liquid Dec. 20, 2012; Actra Biomaterialia; pp. 1-9; 9 (2013); Elsevier; GB.

Kim, Yoontae; Biofabrication of 3D printed hydroxyapatite composite scaffolds for bone regeneration; Mar. 8, 2021; Biomedical Materials; pp. 1-13; 16 (2021); IOP Publishing; US.

Bagnol, Romain; Coaxial micro-extrusion of a calcium phosphate ink with aqueous solvents improves printing stability, structure fidelity and mechanical properties; Mar. 9, 2021; Acta Biomaterialia; pp. 1-11; 16:13; Elsevier, GB.

Raymond, Santiago; Accelerated hardening of nanotextured 3D-plotted self-setting calcium phosphate inks; May 26, 2018; Acta Biomaterialia; pp. 451-462; 75 (2018); Elsevier, GB.

Zhang, Boqing; Porous bioceramics produced by inkjet 3D printing; Effect of printing ink formulation on the ceramic macro and micro porous architectures control; Aug. 13, 2018; Composites Part B; pp. 112-121; 155 (2018) Elsevier, GB.

PCT/US2021/019274; Written Opinion of the ISA/US; dated Mar. 29, 2021; pp. 1-11; US.

PCT/US2021/019274; International Search Report; dated Apr. 22, 2021; pp. 1-2; US.

Roca, R.Y., A. Peura, M.P. Kowaleski, M.T. Watson, M. Lendhey, P.J. Rocheleau, D.A. Hulse, Ex vivo mechanical properties of a 2.5-mm bone anchor for treatment of cranial cruciate ligament rupture in toy breed dogs, Vet. Surg. (2020) 1-5. https://doi.org/10.1111/vsu.13399.

Motherway, J.A., P. Verschueren, G. Van der Perre, J. Vander Sloten, M.D. Gilchrist, The mechanical properties of cranial bone: The effect of loading rate and cranial sampling position, J. Biomech. 42 (2009) 2129-2135. https://doi.org/10.1016/j.jbiomech.2009.05.030.

Kriewall, T.J., Structural, mechanical, and material properties of fetal cranial bone, Am. J. Obstet. Gynecol. 143 (1982) 707-714. https://doi.org/10.1016/0002-9378(82)90119-3.

McElhaney, J.H., J.L. Fogle, J.W. Melvin, R.R. Haynes, V.L. Roberts, N.M. Alem, Mechanical properties of cranial bone, J. Biomech. 3 (1970) 495-511. https://doi.org/10.1016/0021-9290(70)90059-X.

Morgan, E.F., G.U. Unnikrisnan, A.I. Hussein, Bone Mechanical Properties in Healthy and Diseased States, Annu. Rev. Biomed. Eng. 20 (2018) 119-143. https://doi.org/10.1146/annurev-bioeng-062117-121139.

Ramasamy, A., A.M. Hill, S. Masouros, I. Gibb, A.M.J. Bull, J.C. Clasper, Blast-related fracture patterns: A forensic biomechanical approach, J. R. Soc. Interface. 8 (2011) 689-698. https://doi.org/10.1098/rsif.2010.0476.

Gupta, A., N. Kukkar, K. Sharif, B.J. Main, C.E. Albers, S.F. El-Amin, Bone graft substitutes for spine fusion: A brief review, World J. Orthop. 6 (2015) 449-456. https://doi.org/10.5312/wjo.v6.i6.449.

Wolff, J., H. Agata, G.K. Sándor, S. Haimi, Peri-Implant Tissue Findings in Bone Grafted Oral Cancer Patients Compared to non Bone Grafted Patients without Oral Cancer, J. Oral Maxillofac. Res. 2 (2011) 1-8. https://doi.org/10.5037/jomr.2011.2402.

Millikan, P.D. V. Karas, S.S. Wellman, Treatment of osteonecrosis of the femoral head with vascularized bone grafting, Curr. Rev. Musculoskelet. Med. 8 (2015) 252-259. https://doi.org/10.1007/s12178-015-9285-8.

(56) References Cited

OTHER PUBLICATIONS

Goulet, J.A., L.E. Senunas, G.L. DeSilva, M.L.V.H. Greenfield, Autogenous iliac crest bone graft: Complications and functional assessment, Clin. Orthop. Relat. Res. (1997) 76-81. https://doi.org/10.1097/00003086-199706000-00011.

Greenwald, A.S., S.D. Boden, V.M. Goldberg, Y. Khan, C.T. Laurencin, R.N. Rosier, Bone-Graft Substitutes Facts, Fictions, and Applications, J. Bone Jt. Surgery-American vol. 83 (2001) 98-103. https://doi.org/10.2106/00004623-200100022-00007.

Baldwin, P., D.J. Li, D.A. Auston, H.S. Mir, R.S. Yoon, K.J. Koval, Autograft, Allograft, and Bone Graft Substitutes, J. Orthop. Trauma. 33 (2019) 203-213. https://doi.org/10.1097/BOT.0000000000001420.

Grigoryan, B., S.J. Paulsen, D.C. Corbett, D.W. Sazer, C.L. Fortin, A.J. Zaita, P.T. Greenfield, N.J. Calafat, J.P. Gounley, A.H. Ta, F. Johansson, A. Randles, J.E. Rosenkrantz, J.D. Louis-rosenberg, P.A. Galie, K.R. Stevens, J.S. Miller, Multivascular networks and functional intravascular topologies within biocompatible hydrogels, 464 (2019) 458-464.

Miller, J.S., K.R. Stevens, M.T. Yang, B.M. Baker, D.-H.T. Nguyen, D.M. Cohen, E. Toro, A.A. Chen, P.A. Galie, X. Yu, R. Chaturvedi, S.N. Bhatia, C.S. Chen, Rapid casting of patterned vascular networks for perfusable engineered three-dimensional tissues, Nat. Mater. 11 (2012) 768-774. https://doi.org/10.1038/nmat3357.

Lin, N.Y.C., K.A. Homan, S.S. Robinson, D.B. Kolesky, N. Duarte, A. Moisan, J.A. Lewis, Renal reabsorption in 3D vascularized proximal tubule models, Proc. Natl. Acad. Sci. U. S. A. 116 (2019) 5399-5404. https://doi.org/10.1073/pnas.1815208116.

Kolesky, D.B., K.A. Homan, M.A. Skylar-Scott, J.A. Lewis, Three-dimensional bioprinting of thick vascularized tissues, Proc. Natl. Acad. Sci. U. S. A. 113 (2016) 3179-3184. https://doi.org/10.1073/pnas.1521342113.

Chartrain, N.A., C.B. Williams, A.R. Whittington, A review on fabricating tissue scaffolds using vat photopolymerization, Acta Biomater. 74 (2018) 90-111. https://doi.org/10.1016/j.actbio.2018.05.010.

Tan, X.P., Y.J. Tan, C.S.L. Chow, S.B. Tor, W.Y. Yeong, Metallic powder-bed based 3D printing of cellular scaffolds for orthopaedic implants: A state-of-the-art review on manufacturing, topological design, mechanical properties and biocompatibility, Mater. Sci. Eng. C. 76 (2017) 1328-1343. https://doi.org/10.1016/j.msec.2017.02.094.

Liao, H.-T., M.-Y. Lee, W.-W. Tsai, H.-C. Wang, W.-C. Lu, Osteogenesis of adipose-derived stem cells on polycaprolactone-β-tricalcium phosphate scaffold fabricated via selective laser sintering and surface coating with collagen type I, J. Tissue Eng. Regen. Med. 10 (2016) E337-E353.https://doi.org/10.1002/term.1811.

Shim, J.-H., S.E. Kim, J.Y. Park, J. Kundu, S.W. Kim, S.S. Kang, D.-W. Cho, Three-Dimensional Printing of rhBMP-2-Loaded Scaffolds with Long-Term Delivery for Enhanced Bone Regeneration in a Rabbit Diaphyseal Defect, Tissue Eng. Part A. 20 (2014) 1980-1992. https://doi.org/10.1089/ten.tea.2013.0513.

Trombetta, R., J.A. Inzana, E.M. Schwarz, S.L. Kates, H.A. Awad, 3D Printing of Calcium Phosphate Ceramics for Bone Tissue Engineering and Drug Delivery, Ann. Biomed. Eng. 45 (2017) 23-44. https://doi.org/10.1007/s10439-016-1678-3.

Li, X., Y. Yuan, L. Liu, Y.-S. Leung, Y. Chen, Y. Guo, Y. Chai, Y. Chen, 3D printing of hydroxyapatite/tricalcium phosphate scaffold with hierarchical porous structure for bone regeneration, Bio-Design Manuf. 3 (2020) 15-29. https://doi.org/10.1007/s42242-019-00056-5.

Leukers, B., H. Gülkan, S.H. Irsen, S. Milz, C. Tille, M. Schieker, H. Seitz, Hydroxyapatite scaffolds for bone tissue engineering made by 3D printing, J. Mater. Sci. Mater. Med. 16 (2005) 1121-1124. https://doi.org/10.1007/s10856-005-4716-5.

Fahimipour, F., M. Rasoulianboroujeni, E. Dashtimoghadam, K. Khoshroo, M. Tahriri, F. Bastami, D. Lobner, L. Tayebi, 3D printed TCP-based scaffold incorporating VEGF-loaded PLGA microspheres for craniofacial tissue engineering, Dent. Mater. 33 (2017) 1205-1216. https://doi.org/10.1016/j.dental.2017.06.016.

Bruyas, A., F. Lou, A.M. Stahl, M. Gardner, W. Maloney, S. Goodman, Y.P. Yang, Systematic characterization of 3D-printed PCL/β-TCP scaffolds for biomedical devices and bone tissue engineering: Influence of composition and porosity, J. Mater. Res. 33 (2018) 1948-1959. https://doi.org/10.1557/jmr.2018.112.

Wen, Y., S. Xun, M. Haoye, S. Baichuan, C. Peng, L. Xuejian, Z. Kaihong, Y. Xuan, P. Jiang, L. Shibi, 3D printed porous ceramic scaffolds for bone tissue engineering: a review, Biomater. Sci. 5 (2017) 1690-1698. https://doi.org/10.1039/C7BM00315C.

Touri, M., F. Moztarzadeh, N.A.A. Osman, M.M. Dehghan, M. Mozafari, 3D-printed biphasic calcium phosphate scaffolds coated with an oxygen generating system for enhancing engineered tissue survival, Mater. Sci. Eng. C. 84 K2018) 236-242. https://doi.Org/10.1016/j.msec.2017.11.037.

Dong, L., S.J. Wang, X.R. Zhao, Y.F. Zhu, J.K. Yu, 3D-printed poly (e-caprolactone) scaffold integrated with cellladen chitosan hydrogels for bone tissue engineering, Sci. Rep. 7 (2017) 4-12. https://doi.org/10.1038/s41598-017-13838-7.

Donate, R., Z. Ortega, L. Wang, V. Ribeiro, D. Pestana, M. Joaquim, R.L. Reis, Comparison between calcium carbonate and β-tricalcium phosphate as additives of 3D printed scaffolds with polylactic acid matrix, J. Tissue Eng. Regen. Med. (2019) 0-2. https://doi.org/10.1002/term.2990.

Qian, C., F. Zhang, J. Sun, Fabrication of Ti/HA composite and functionally graded implant by three- dimensional printing, Biomed. Mater. Eng. 25 (2015) 127-136. https://doi.org/10.3233/BME-151263.

Liu, J., Ruan, L. Chang, H. Yang, W. Ruan, Porous Nb—Ti—Ta alloy scaffolds for bone tissue engineering: Fabrication, mechanical properties and in vitro/vivo biocompatibility, Mater. Sci. Eng. C. 78 (2017) 503-512. https://doi.org/10.1016/j.msec.2017.04.088.

Wieding, J., A. Jonitz, R. Bader, The effect of structural design on mechanical properties and cellular response of additive manufactured titanium scaffolds, Materials (Basel). 5 (2012) 1336-1347. https://doi.org/10.3390/ma5081336.

De Giglio, E., M.A. Bonifacio, A.M. Ferreira, S. Cometa, Z.Y. Ti, A. Stanzione, K. Dalgarno, P. Gentile, Multi-compartment scaffold fabricated via 3D-printing as in vitro co-culture osteogenic model, Sci. Rep.8 (2018) 15130. https://doi.org/10.1038/s41598-018-33472-1.

Bittner, S.M., B.T. Smith, L. Diaz-Gomez, C.D. Hudgins, A.J. Melchiorri, D.W. Scott, J.P. Fisher, A.G. Mikos, Fabrication and mechanical characterization of 3D printed vertical uniform and gradient scaffolds for bone and osteochondral tissue engineering, Acta Biomater. 90 (2019) 37-48. https://doi.org/10.1016/j.actbio.2019.03.041.

Cao, Y., L. Xiao, Y. Cao, A. Nanda, C. Xu, Q. Ye, 3D printed β-TCP scaffold with sphingosine 1-phosphate coating promotes osteogenesis and inhibits inflammation, Biochem. Biophys. Res. Commun. 512 (2019) 889-895. https://doi.org/10.1016/j.bbrc.2019.03.132.

Ishikawa, K., Takagi, L.C. Chow, K. Suzuki, Reaction of calcium phosphate cements with different amounts of tetracalcium phosphate and dicalcium phosphate anhydrous, J. Biomed. Mater. Res. 46 (1999) 504-510. https://doi.org/10.1002/(SICI)1097-4636(19990915)46:4<504:AID-JBM8>3.0.CQ;2-H.

Shimada, A., T. Medical, L.C. Chow, S. Takagi, J. Tagami, Properties of Injectable Apatite-Forming Premixed Cements, J. Res. Natl. Inst. Stand. Technol. 115 (2010) 233-241.

Park, Su A., Su Her Lee, Wan Dou Kim, Fabrication of porous polycaprolactone/hydroxyapatite (PCL/HA) blend scaffolds using a 3D plotting system for bone tissue engineering, Bioprocess Biosyst Eng., Springer, 34:505-513.

Zhou, S., Y.B. Li, Y.Y. Wang, Y. Zuo, S.B. Gao, M. Li, L. Zhang, The porous structure and mechanical properties of injection molded HA/PA66 scaffolds, Int. Polym. Process. 29 (2014) 454-460. https://doi.org/10.3139/217.2851.

Moncal, K.K., D.N. Heo, K.P. Godzik, D.M. Sosnoski, O.D. Mrowczynski, E. Rizk, V. Ozbolat, S.M. Tucker, E.M. Gerhard, M. Dey, G.S. Lewis, J. Yang, I.T. Ozbolat, 3D printing of poly(ϵ-caprolactone)/poly(D,L-lactide-co-glycolide)/hydroxyapatite composite constructs for bone tissue engineering, J. Mater. Res. 33 (2018) 1972-1986. https://doi.org/10.1557/jmr.2018.111.

(56) References Cited

OTHER PUBLICATIONS

Alghunaim, A., S. Kirdponpattara, B.M.Z. Newby, Techniques for determining contact angle and wettability of powders, Powder Technol. 287 (2016) 201-215. https://doi.org/10.1016/j.powtec.2015.10.002.

Mirzababaei, S., S. Pasebani, A Review on Binder Jet Additive Manufacturing of 316L Stainless Steel, J. Manuf. Mater. Process. 3 (2019) 82. https://doi.org/10.3390/jmmp3030082.

Jariwala, S.H., G.S. Lewis, Z.J. Bushman, J.H. Adair, H.J. Donahue, 3D Printing of Personalized Artificial Bone Scaffolds, 3D Print. Addit. Manuf. 2 (2015) 56-64. https://doi.org/10.1089/3dp.2015.0001.

Detsch, R., S. Schaefer, U. Deisinger, G. Ziegler, H. Seitz, B. Leukers, In vitro—Osteoclastic Activity Studies on Surfaces of 3D Printed Calcium Phosphate Scaffolds, J. Biomater. Appl. 26 (2011) 359-380. https://doi .org/10.1177/0885328210373285.

Wang, Z., A.A. Volinsky, N.D. Gallant, Nanoindentation study of polydimethylsiloxane elastic modulus using berkovich and flat punch tips, J. Appl. Polym. Sci. 132 (2015) 1-7. https://doi.org/10.1002/app.41384.

Kim, J.W., K.H. Shin, Y.H. Koh, M.J. Hah, J. Moon, H.E. Kim, Production of poly($\epsilon$- caprolactone)/hydroxyapatite composite scaffolds with a tailored macro/micro-porous structure, high mechanical properties, and excellent bioactivity, Materials (Basel). 10 (2017). https://doi.org/10.3390/ma10101123.

Wang, Y., Y. Xue, J. Wang, Y. Zhu, Y. Zhu, X. Zhang, J. Liao, X. Li, X. Wu, Y.X. Qin, W. Chen, A composite hydrogel with high mechanical strength, fluorescence, and degradable behavior for bone tissue engineering, Polymers (Basel). 11 (2019). https://doi.org/10.3390/polym11071112.

Alizadeh-OSGouei, M., Y. Li, C. Wen, A comprehensive review of biodegradable synthetic polymer-ceramic composites and their manufacture for biomedical applications, Bioact. Mater. 4 (2019) 22-36. https://doi.org/10.1016/j.bioactmat.2018.11.003.

Akkineni, A.R., Y. Luo, M. Schumacher, B. Nies, A. Lode, M. Gelinsky, 3D plotting of growth factor loaded calcium phosphate cement scaffolds, Acta Biomater. 27 (2015) 264-274. https://doi.Org/10.1016/j.actbio.2015.08.036.

Sohn, H.S., J.K. Oh, Review of bone graft and bone substitutes with an emphasis on fracture surgeries, Biomater. Res. 23 (2019) 4-10. https://doi.org/10.1186/s40824-019-0157-y.

Xu, H.H.K., P. Wang, L. Wang, C. Bao, Q. Chen, M.D. Weir, L.C. Chow, L. Zhao, X. Zhou, M.A. Reynolds, Calcium phosphate cements for bone engineering and their biological properties, Bone Res. 5 (2017) 17056. https://doi.org/10.1038/boneres.2017.56.

Chow, L.C., Next generation calcium phosphate-based biomaterials., Dent. Mater. J. 28 (2009) 1-10. https://doi.org/10.4012/dmj.28.1.

Jancar, J., A. Sloviková, E. Amler, P. Krupa, H. Kecová, L. Plánka, P. Gál, A. Nečas, Mechanical response of porous scaffolds for cartilage engineering, Physiol. Res. 56 (2007).

Poh, P.S.P, D. Valainis, K. Bhattacharya, M. van Griensven, P. Dondl, Optimization of Bone Scaffold Porosity Distributions, Sci. Rep. 9 (2019) 1-10. https://doi.org/10.1038/s41598-019-44872-2.

Lakatos, É., Magyar, I. Bojtár, Material properties of the mandibular trabecular bone, J. Med. Eng. 2014 (2014). https://doi.org/10.1155/2014/470539.

\* cited by examiner

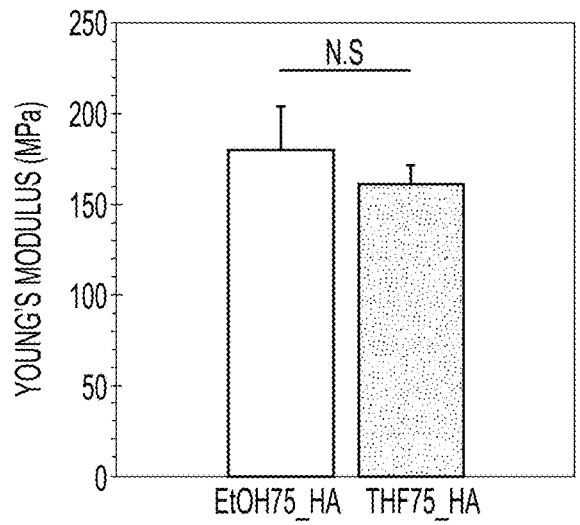
FIG. 8B
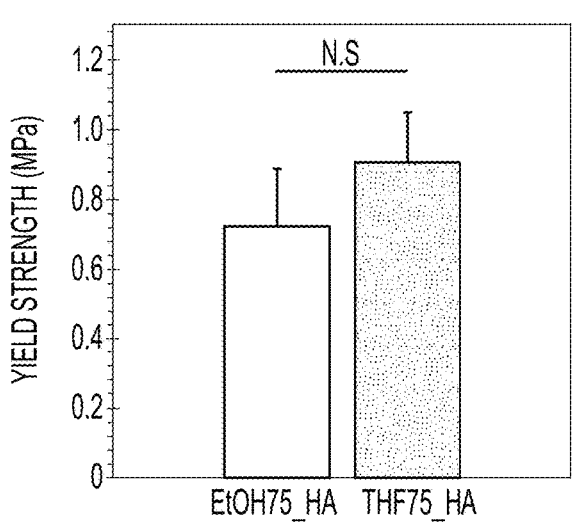
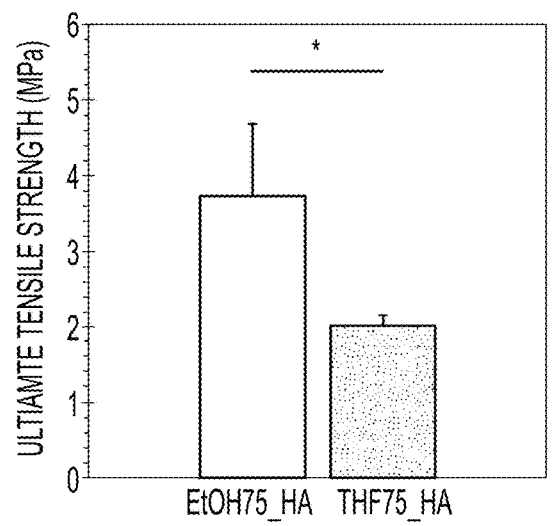
FIG. 8C     FIG. 8D

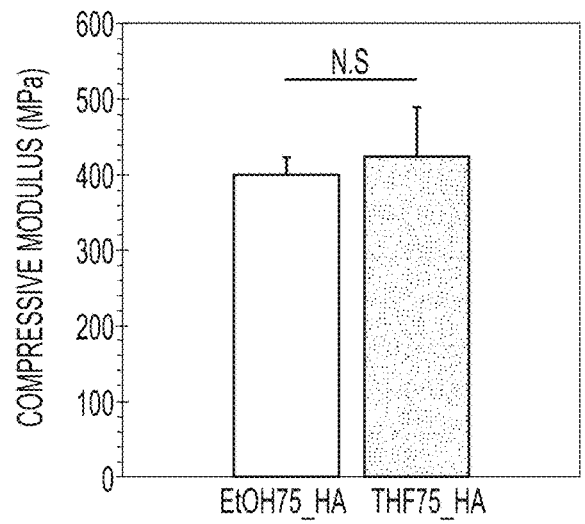
FIG. 9B
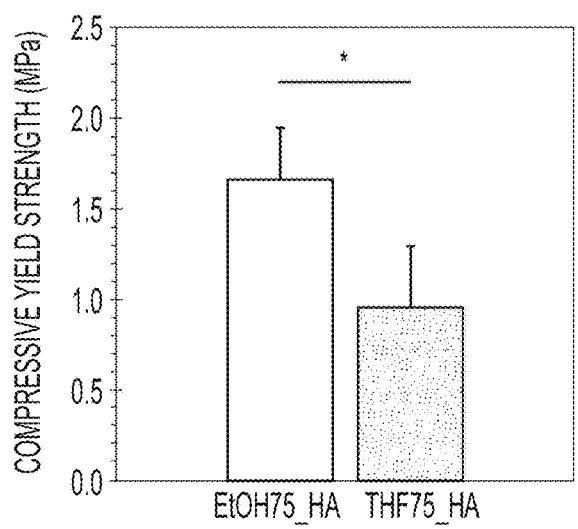 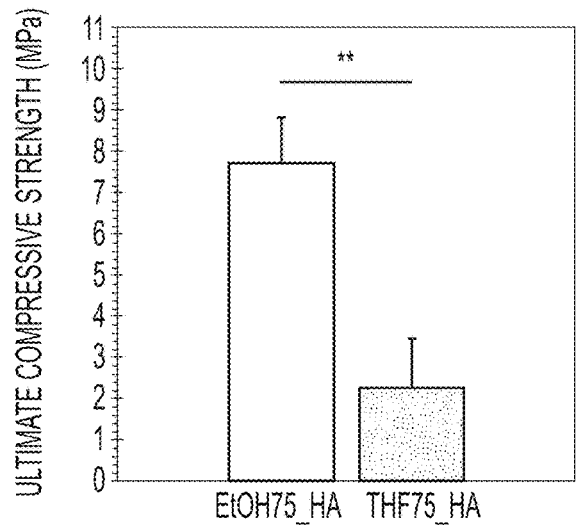
FIG. 9C  FIG. 9D

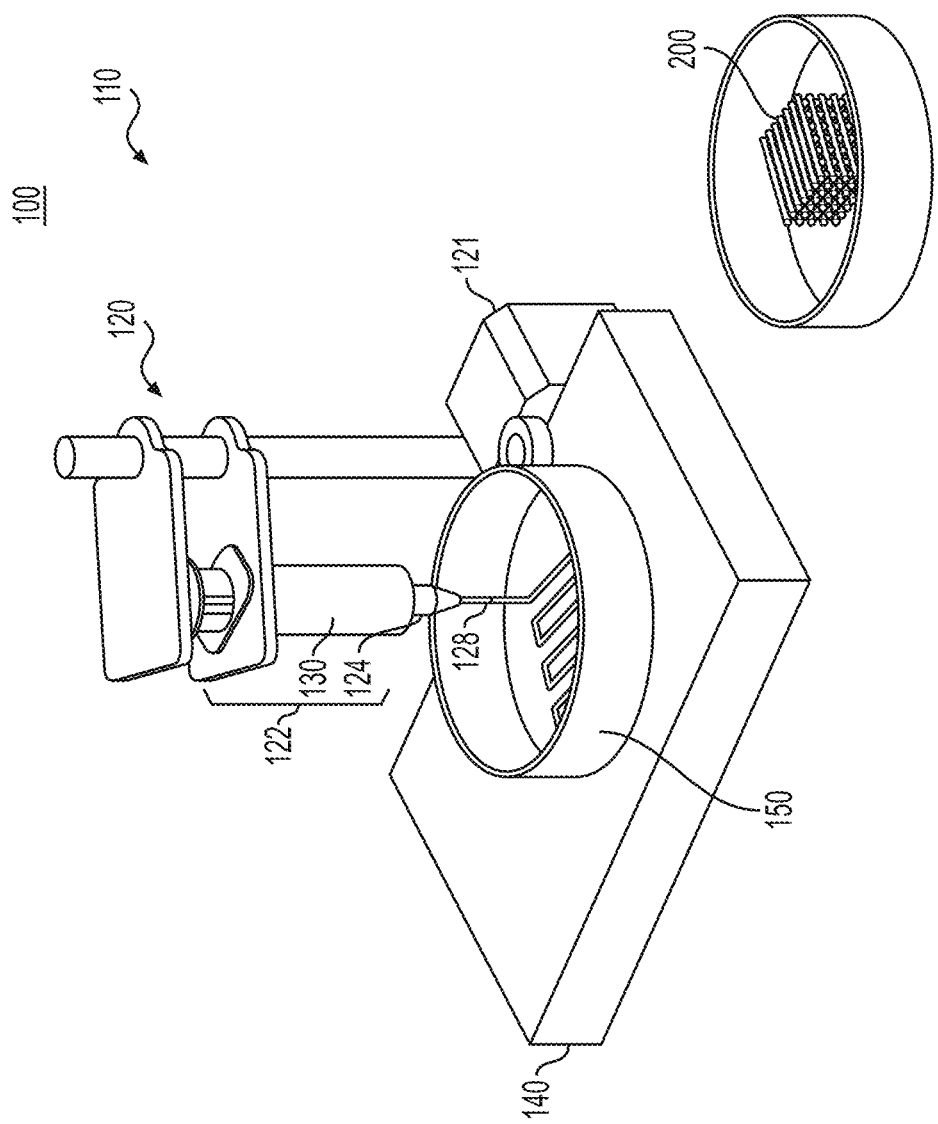

THREE-DIMENSIONAL PRINTED HYDROXYAPATITE COMPOSITE SCAFFOLDS FOR BONE REGENERATION, PRECURSOR COMPOSITIONS AND METHODS OF PRINTING

RELATED APPLICATIONS

This application claims priority to provisional patent application 62/981,070, filed Feb. 25, 2020, entitled "Three-Dimensional Printed Hydroxyapatite Composite Scaffolds for Bone Regeneration," the disclosure of which is incorporated by reference.

BACKGROUND

A bone graft is a surgical procedure to repair, through tissue replacement and regeneration, bones or joints damaged by or the result of trauma [1], spinal fusion [2], tumor excision [3], and avascular necrosis [4]. Bone grafts replace missing or damaged bone to provide structural stability of a patient's body, for example, the jawbone. Autografts and allografts are the two most common types. An autograft is bone tissue that is transferred from one part of a patient's body to another part. They are histocompatible and non-immunogenic, and they offer all the imperative properties required of a bone graft material, such as osteoinduction, osteogenesis, and osteoconductivity. Although bone autografts are the standard treatment, they are limited in supply with extended operation procedures and are related to donor site morbidity. Apart from autografts, allografts represent one of the most common bone-grafting techniques. An allograft is bone tissue that is transplanted from one person to another. Allografts typically come from a living donor or a cadaver. Allografts are safe, ready to use, and available in large amounts. Allografts do not require additional surgical time for harvest and lead to a quicker recovery than may occur with an autograft. However, allografts do not have any cellular bone component because they are devitalized via irradiation or freeze-drying process leading to reduced osteoinductive properties. Finally, allografts are associated with risks of immunoreactions and transmission of infections [5-7].

Recent developments in bone tissue engineering have led to the use of artificial bone scaffolds as an adjunct to autografts and allografts, and other forms of bone grafts. These developments may incorporate additive biomanufacturing to when fabricating biomimetic and complex organ structures [8-11]. For example, synthetic scaffolds may be used to stimulate bone repair. Such scaffolds may be designed to be biocompatible and exhibit porosity, mechanical properties, and osteoconductivity similar to those of native tissue. The scaffolds may have a specific form or geometry. Such scaffolds have been made through casting, mold, and electrospinning. More recently, scaffolds have been produced through three-dimensional (3D) printing, which has the advantage of producing a patient-specific geometry that may be derived, for example, from a computed tomography (CT) scan. Three-dimensional printing processes that include vat polymerization [12], powder bed fusion [13,14], material extrusion [15,16], and binder jetting [17], at low or high temperature, have been used for such bone substitute fabrication. Bioceramic materials, including hydroxyapatite (HA) [18], β-tricalcium phosphate (β-TCP) [19,20], α-tricalcium phosphate (α-TCP) [21,22] combined with synthetic polymers, such as poly (ε-caprolactone) (PCL) [23,24], or metals (Titanium (Ti)) [25-27], have been used [28-30]. However, current 3D printing processes for fabricating scaffolds suffer from significant deficiencies and thus are not able to produce high-resolution, biocompatible scaffolds. For example, current 3D printing methods are low-resolution processes, and are incapable of printing scaffolds with filament resolutions less than 200 μm. Furthermore, with current 3D printing processes, the amount of ceramic material in the printing inks is less than 75% of the total, which results in printed scaffolds having low elasticity and low tensile and compressive strengths. Finally, the scaffolds are not printed at room temperature (RT) (i.e., 20-36° C.). Rather, the scaffolds typically are printed at much higher temperatures; temperatures sufficient to prevent the viability of cells during the printing process. As a consequence, and as described herein, current 3D-printed scaffolds lack many bio-related advantages.

SUMMARY

Disclosed are 3D-printed scaffolds having high hydroxyapatite (HA) content. The disclosed methods and compositions provide the ability to print biocompatible scaffolds having patient-specific geometries with controlled porosity, microstructure, osteoconductivity, and mechanical strength. The scaffolds may be used for in vitro and in vivo craniofacial and dental applications. Scaffolds having various shapes and sizes may be obtained by use of herein disclosed modifications in order to meet desired mechanical properties required by differing applications. In an aspect, the scaffolds may be used for bone grafting and regeneration in humans.

The disclosed biocompatible 3D-printed scaffolds may be bioactive, osteoconductive, and biodegradable. These properties make the herein disclosed 3D-printed scaffolds useable for cell growth with greater efficacy and better predictability than is possible with current 3D scaffold printing methods. In an embodiment, the 3D-printed scaffolds may be printed along with living cells to generate cell-driven, functional tissue. Such a scaffold can be used in a human defect as a cell delivery mechanism. Furthermore, because of the fine resolution achievable with the herein disclosed methods, biomaterials may be deposited precisely in the scaffold to achieve a desired distribution, uniform or non-uniform. The 3D printing process may incorporate encapsulation of the biomaterials to prevent damage that otherwise might occur during the scaffold material setting processes and from other interactions with components of slurries used in the printing process.

The herein disclosed scaffolds may be formulated from non-aqueous Calcium Phosphate Cement (CPC) slurries as 3D printing inks; the CPC slurries may include a $Na_2HPO_4$ solution as a hardening accelerator. Three-dimensional printing in a $Na_2HPO_4$ bath helps avoid printer nozzle clogging resulting from possible rapid solvent evaporation at the nozzle tip. The amount of $Na_2HPO_4$ in the bath may be adjusted to control the hardening speed of the slurries. All 3D printing at room temperature was performed, thereby allowing the use of a motor-driven syringe extruder with its working temperature (i.e., room temperature) rather than a hot-melting pneumatic extruder (60-350° C.).

The evaporation speed of polymer-solvents such as Tetrahydrofuran (THF) and Ethanol (EtOH) affect the rheological properties, which are strongly related to the material printability. The viscosity of the CPC slurries may increase while the slurries load into the empty syringe; accordingly, slurry loading time may be minimized to avoid unwanted increases in slurry viscosity.

To print a scaffold according to a specific geometry and form for a specific application, the feed composition and movement of the injection nozzle are controlled by a computer executing a program of instructions.

In an embodiment, a computer-controlled method for room temperature 3D printing a biocompatible, composition controlled scaffold includes preparing a solid phase composition comprising a calcium phosphate cement powder; preparing a liquid phase composition comprising a dissolved polymer material; homogeneously mixing the solid phase composition and the liquid phase composition to create a homogeneous, bio-compatible slurry; disposing the slurry in a reservoir system coupled to a printing nozzle system, the printing nozzle system comprising at least one printing nozzle; submerging a printing substrate in a liquid bath disposed below the printing nozzle; under control of a computer, operating a motor to extrude the slurry, at room temperature, from the reservoir system through the printing nozzle system and to cause relative x, y, and z displacement between the printing nozzle system and the printing substrate; employing a hardening accelerator to assist formation of the biocompatible, composition controlled scaffold; and maintaining the 3D printing scaffold fully submerged in the liquid bath during the entire 3D printing process.

In an embodiment, a three-dimensional, biocompatible scaffold precursor composition for forming a bio-compatible polymer/hydroxyapatite composite scaffold includes a slurry and a hardening accelerator. The slurry includes a solid phase formed from mixing, in an embodiment, approximately 73% w/w tetracalcium phosphate (TTCP; $Ca_4(PO_4)_2O$) and approximately 27% w/w dicalcium phosphate anhydrous (DCPA; $CaHPO_4$), and a liquid phase formed from dissolving a polymer in a solvent. Here, approximately may refer to the capability to measure the solid phase compounds; alternately, approximately may refer to what is considered normal measurement practice in the art; alternately, approximately may refer to within 1 (one) percent (e.g., 72% to 74%). In other embodiments, the solid phase may be composed of tetracalcium phosphate and dicalcium phosphate anhydrous having weight ratios less than approximately 73:27 and as low as approximately 20:80. In an embodiment, the solvent may be Ethanol (EtOH) and Tetrahydrofuran (THF). In an embodiment, the solid to liquid phases have a weight ratio of 0.75 to 1. In other embodiments, the weight ratio may range from 0.1 to 1 up to 2 to 1. The hardening accelerator may be introduced during printing of the polymer/hydroxyapatite composite scaffold. In an embodiment, the hardening accelerator is introduced into an aqueous or non-aqueous bath in which the scaffold is printed. In another embodiment, the hardening accelerator is mixed with the slurry. In an embodiment, the hardening accelerator is disodium phosphate ($N_2HPO_4$).

A three-dimensional, biocompatible scaffold precursor composition for room-temperature printing a bio-compatible polymer/hydroxyapatite composite scaffold includes a room-temperature slurry, comprising a mixture of a sold phase that includes a mixture of tetracalcium phosphate (TTCP; $Ca_4(PO_4)_2O$) and dicalcium phosphate anhydrous (DCPA; $CaHPO_4$), and a liquid phase that includes a polymer in a solvent. The solvent may be Ethanol (EtOH) or Tetrahydrofuran (THF), and the polymer may be polyvinyl butyral (PVB), polycaprolactone (PCL), or poly lactic-co-glycolic acid (PLGA). A hardening accelerator added to the slurry during room-temperature printing of the polymer/hydroxyapatite composite scaffold.

A computer-controlled method for room-temperature printing a composition-controlled product using 3D printing, includes disposing a liquid reactant composition in a reservoir, the liquid reactant composition comprising a mixture of: a solid phase comprising a calcium phosphate cement (CPC) powder, and a liquid phase comprising a polymer material dissolved in a solvent, the polyvinyl material selected from a group consisting of polyvinyl butyral (PVB) and polycaprolactone (PCL), the solvent selected from a group consisting of Ethanol (EtOH) and Tetrahydrofuran (THF); at room temperature, extruding the liquid reactant composition by a computer controlling a motor-driven syringe extruder having an exit nozzle of diameter less than or equal to 210 microns; scanning, under control of the computer, a liquid reactant exit nozzle over a substrate while maintaining the substrate fully submerged in an aqueous bath; and depositing the liquid reactant composition onto the substrate, wherein the solvent evaporates to produce, under influence of a hardening accelerator, a biocompatible hydroxyapatite/polymer composite scaffold.

DESCRIPTION OF THE DRAWINGS

The detailed description refers to the following figures in which like numerals refer to like objects, and in which:

FIGS. 8A-8D presents characterizations of mechanical properties of the PVB/HA scaffolds under tension;

FIGS. 9A-9D present measurements of mechanical properties of the PVB/HA scaffolds under compression;

FIG. 15 illustrates an example system for 3D printing of a biocompatible polymer/hydroxyapatite composite scaffold.

DETAILED DESCRIPTION

Applicants have invented a novel and nonobvious biofabrication method for three-dimensional (3D) printing of polyvinyl butyral/hydroxyapatite (PVB/HA) biocompatible composite scaffolds. In an embodiment, the novel and nonobvious biofabrication methods disclosed herein are based on 3D printing of calcium phosphate cement (CPC) slurries (sometimes referred to as bio-inks) in an aqueous solution bath containing, in an aspect, sodium phosphate dibasic ($Na_2HPO_4$). Applicants formulated the CPC slurries by mixing CPC powder (solid phase) and two different types of PVB-dissolved solutions (liquid phase). In an embodiment, the CPC powder was mixed approximately 73% w/w tetracalcium phosphate (TTCP; $Ca_4(PO_4)_2O$) and approximately 27% w/w dicalcium phosphate anhydrous (DCPA; $CaHPO_4$). In other embodiments, other weight ratios were used. The PVB-dissolved solutions were prepared by dissolving PVB polymer in an Ethanol (EtOH) solvent or a Tetrahydrofuran (THF) solvent. Generally, 3D printing of such CPC slurries would be difficult because of (1) the high viscosity with a large amount (75 and 100 wt %) of the CPC powder present, and (2) the rapid evaporation of the solvent. Applicants overcame these difficulties by 3D printing using a CPC slurry in an aqueous environment to form a solid HA structure, and further by accelerating HA hardening. In an embodiment, applicants used a motor-driven syringe extruder with small nozzles (e.g., diameters: 210 μm) to fabricate PVB/HA composite scaffolds, and all processes were carried out at room temperature. The PVB/HA composite scaffolds were successfully fabricated and tailored according to various periodic patterns regardless of which PVB solvent (EtOH or THF) was used for dissolving the PVB. Applicants tested the osteo-conductivity of the PVB/HA composite scaffolds using Alkaline phosphatase (ALP), Alzarin Red (AR), and Von Kossa (VK). Cells cultured on EtOH75_HA scaffolds under mineralization conditions showed higher mineralization (~2-fold) than cells cultured on THF75_HA scaffolds.

Three-dimensional printing using the herein disclosed printing methods and the CPC slurries and $Na_2HPO_4$ solution makes possible formation, in situ, of hydroxyapatite composite scaffolds at room temperature using syringe nozzle with a diameter of 210 μm or smaller. Advantages of room temperature (i.e., 20-36° C.) printing are disclosed herein. The methods and materials disclosed herein are compatible with many commercially available bioprinters commonly used in biofabrication and may be adapted to better replicate architectural and compositional requirements of individual tissues that are possible with traditional scaffold printing methods. In an embodiment, the PVB polymer may be replaced by Polycaprolactone (PCL).

Hypothesis, Experimental Approach, and Summary of Results

Figure 2:
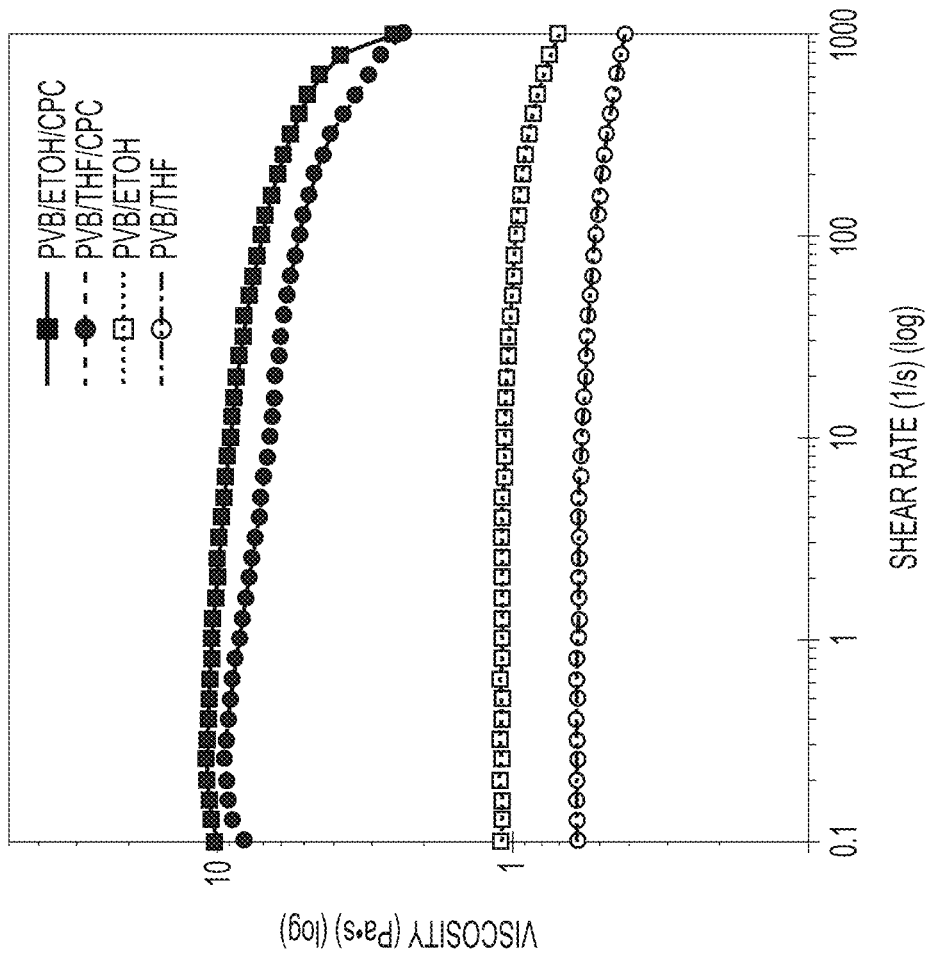
FIG. 2 illustrates the viscosity (η) of different PVB/CPC slurries as a function of shear rate (1/s)
Figure 7A:
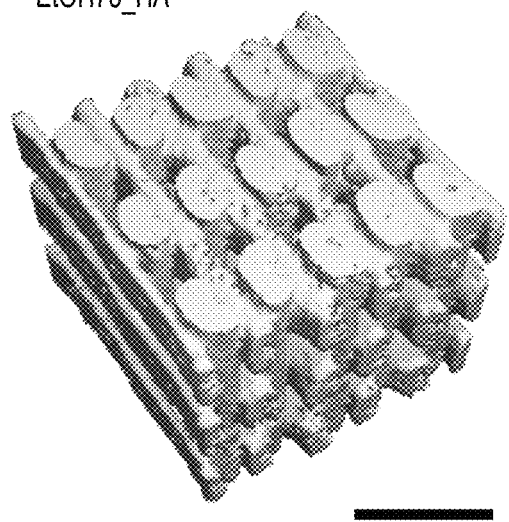
FIGS. 7A-7B present images of PVB/HVA scaffolds.
Figure 7B:
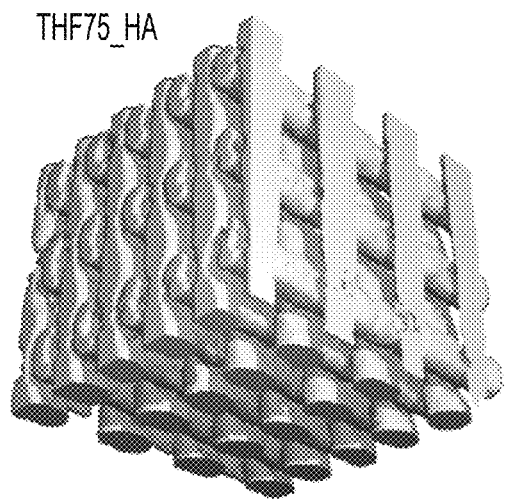
Figure 7C:
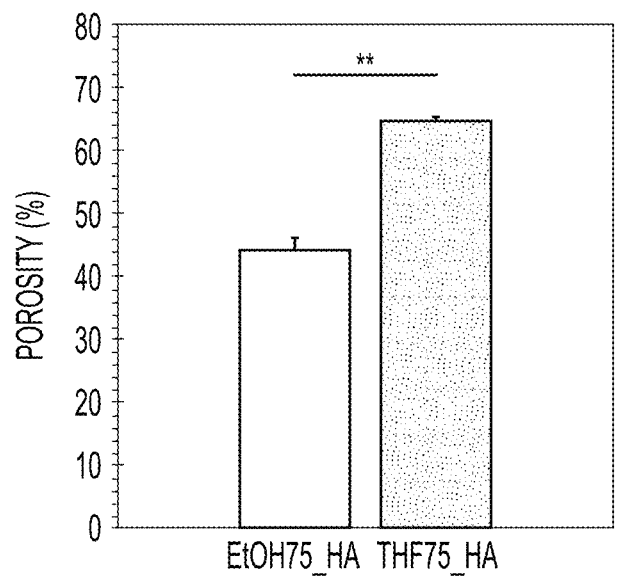
FIG. 7C presents calculated porosities of the PVB/HA scaffolds of FIGS. 7A and 7B.
Figure 7D:
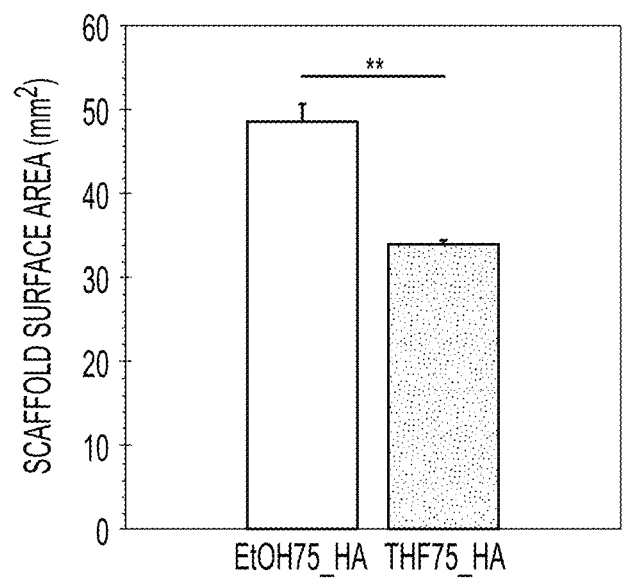
FIG. 7D presents calculated surface areas of the PVB/HA scaffolds of FIGS. 7A and 7B.

Recognizing that bone grafts made of a bioceramic material would be of importance for successful implantation and rapid osteointegration, and that additive manufacturing offers the ability to fabricate HA scaffolds with defined macroporosity and improved mechanical properties, applicants engineered 3D printed in situ-formed HA scaffolds using a rapid 3D printing procedure at room temperature. Applicants discovered that printing of TTCP/DCPA in a $Na_2HPO_4$ bath results in the formation of HA in situ while avoiding conventional methods of HA coating of a scaffold surface and HA printing at high temperatures [29, 33-35]. Applicants methods produced cell-integrated 3D printed scaffolds with controlled HA formation. In these methods, material printability is related to many parameters including particle size and size distribution, morphology and surface area of the powder, roughness and the ability of the powder to flow from an extruder (flowability) of the powders, solubility/wettability/reactivity of the powder with the binder, such as PVB polymer [36,37]. Several studies have shown that mean particle sizes of TCP particles in the range of 20-35 μm resulted in good 3D printing accuracy [38,39]. Although they have better flowability, larger particles tend to yield non-uniform layers of filaments leading to low resolution (filament size >200 μm) scaffolds. Applicants overcame this limitation by using a smaller-sized (~5 μm) TTCP particles, which stabilized powder bed homogeneity and yielded high-resolution 3D printed scaffolds. Additionally, the literature reports that the presence of solvent/polymer [20,28,29,40-43] in HA slurries reduced the homogeneity of the slurries and, consequently, homogeneity of the printed scaffolds. To address this issue, applicants used a PVB-dissolved (25% w/v) solution-based slurries for printing. The PVB/EtOH and PVB/THF solutions control the homogeneity of the slurries, thereby avoiding CPC particle separation and aggregation during scaffold printing. PVB/EtOH and PVB/THF solutions without CPC showed Newtonian behavior, while at high shear rates (>100 1/s), the solutions turned into shear-thinning fluids. The presence of CPC in the PVB/EtOH and PVB/THF solutions (i.e., the EtOH75 and THF75 slurries), changed this rheological profile, showing shear-thickening behavior at low shear rates (<0.25 1/s), while the behavior changed to shear-thinning behavior with increasing shear rates. Interestingly, the THF75 slurry showed slight fluctuations in the middle range of the shear rate, indicating some inhomogeneity within the slurry. This rheological profile (FIG. 2) of the EtOH75 and THF75 slurries further provides a controllable and consistent printing process that avoids inconsistencies an inhomogeneities. The PVB polymer also plays an important role in the ultimate tensile strength (UTS) and the ultimate compressive strength (UCS) of the printed scaffolds, which confirms the elastomeric properties of the scaffolds. The CPC reaction with $Na_2HPO_4$ solution in the bath during printing led to HA in situ formation. Studies show that CPCs are promising for clinical applications due to their advantageous properties including bioactivity, osteoconductivity, injectability, and moldability [44,45]. The solubility behavior of TTCP and DCPA was higher, as much as 70-100 times higher than HA at neutral pH. This gives the ability to form HA in situ through a room temperature dissolution-precipitation reaction [46,47]. The ability to 3D print CPC could produce engineered scaffolds with designed mechanical properties and HA scaffolds for tissue regeneration applications, such as spinal and craniofacial injuries. For example, the herein disclosed EtOH75_HA and THF75_HA 3D printed scaffolds exhibited differences in mechanical properties and scaffold shape. The EtOH75 slurry formed larger diameter filaments with large pores compared to THF75 slurry filaments, leading to a 40% larger scaffold surface area (FIG. 7D). The major reason for the differences between the EtOH75 and THF75 filaments is the evaporation during the printing process. The THF vapor pressure (132 mm Hg) is ~3 fold higher than the EtOH (37 mm Hg) one, indicating that THF evaporates faster than the EtOH, leading to smaller pores in the scaffold. Although pore size is small in THF75 filaments, the overall percentage THF75_HA scaffold porosity is ~1.5 times higher than that of the EtOH75_HA scaffold (FIG. 7C). Additionally, studies have demonstrated the effect of porosity on elastic modulus of the scaffolds [27,48,49]. Similarly, the THF75_HA scaffold demonstrated ~50% lower UTS and UCS, indicating that porosity may control the elastomeric properties of the scaffold. The porosity and the filament dimension of the scaffolds control the osteogenic and mineralization potential of the cells. Specifically, the cells formed on EtOH75_HA scaffolds showed higher mineralization potential since they might spread and proliferate on the large filaments and between the large pores, resulting in a 2-fold increase in mineral deposition as shown by Von Kossa staining. Gene expression analysis of specific markers involved in osteoblast (OBST) adhesion and bone matrix syntheses, such as OCN, COL1A2, and integrin β3 (ITGB3) showed higher expression on EtOH75_HA than THF75_HA scaffolds.

In embodiments, polymers that may have high solubility with the solvent in the slurry and low solubility in the hardening accelerator bath and that may be used to produce the herein disclosed HA scaffolds include:

PVB dissolved in: acetic acid, acetone, methanol, Ethanol, 2-propanol, butanol, 2-butoxyethanol, cyclohexanone, benzyl alcohol, 1-methoxy-propanol-2, butyl glycol, n-butyl, acetate, ethyl acetate, N,N-dimethylacetamide, N,N-dimethylformamide, N,N-dimethylsulfoxide, NMP, and THF.

Polycaprolactone (PCL) dissolved in: THF, chloroform, dichloromethane, carbon tetrachloride, benzene, toluene, cyclohexanone and 2-nitropropane, acetone, 2-butanone, ethyl acetate, dimethylformamide, and acetonitrile.

Poly Lactic-co-Glycolic acid (PLGA) dissolved in: THF, acetone, ethyl acetate, and chlorinated solvents.

Poly-L-lactic acid (PLLA) dissolved in: chloroform, dichloromethane (DCM).

Poly(ethylene glycol) (Solid PEG) dissolved in: acetone, dichloromethane, ethanol (95%), methanol. (Liquid PEGs) dissolved in: acetone, alcohols, benzene, glycerin, and glycols.

Polyvinyl pyrrolidone (PVP) dissolved in: methanol, Ethanol.

Polyacrylic acid (PAA) dissolved in: THF, methanol, Ethanol.

Poly(methyl methacrylate) (PMMA) dissolved in: Toluene, Dichloromethane, Chloroform, and Acetone.

Polyoxazoline, polyphosphoesters (PPE): THF, acetonitrile, chloroform, ethyl acetate (based on different type of PPE: Poly((lactide-co-ethylene glycol)-co-ethyloxyphosphate)).

Dextran: methyl sulfide, formamide, ethylene glycol, and glycerol.

The following table (Table 1) shows CPC powders with ratios of TTCP to DCPA in a range from 0.25 to 2.7 (and corresponding weight percentages and molar ratios) that may be prepared fin various embodiments for 3D-printing HA scaffolds:

TABLE 1

| TTCP:DCPA (%) | TTCP/DCPA | Molar Ca/P ratio |
|---|---|---|
| 73:27 | 2.70 | 1.90 |
| 67:33 | 2.00 | 1.80 |
| 60:40 | 1.50 | 1.75 |
| 50:50 | 1.00 | 1.67 |
| 40:60 | 0.67 | 1.57 |
| 33:67 | 0.50 | 1.50 |
| 29:71 | 0.40 | 1.44 |
| 25:75 | 0.33 | 1.40 |
| 22:78 | 0.29 | 1.36 |
| 20:80 | 0.25 | 1.33 |

In embodiments, the herein disclosed CPC slurries may be formulated by mixing a CPC powder and a polymer solution in ratios of a range of about 0.1 to 1.0 CPC powder to liquid up to about 2:1 powder to liquid, as shown in the table (Table 2) below. Printability of the CPC slurries depends on the CPC powder to liquid ratio. The different CPC powder to liquid ratios will lead to either Newtonian or non-Newtonian behavior of the slurry thereby increasing or reducing (or creating non-uniformities), respectively, the filament printing resolution.

TABLE 2

| CPC powders (gram) | Polymer solution (gram) | CPC powder to liquid ratio |
|---|---|---|
| 1 | 10 | 0.1:1 |
| 2 | 10 | 0.2:1 |
| 5 | 10 | 0.5:1 |
| 7.5 | 10 | 0.75:1 |
| 10 | 10 | 1:1 |
| 15 | 10 | 1.5:1 |
| 20 | 10 | 2:1 |

In an embodiment, the CPC slurries (CPC powder+polymer solutions) may be printed in an aqueous environment to better form HA and to improve the hardening process. Hardening time depends on the chemicals and the concentration of the hardening accelerator in the aqueous solution. The hardening accelerators may have the following specifications: a) printed polymer in a CPC/polymer slurry may be insoluble to the hardening solution, b) the accelerators may have pH (2-12) to form HA during the printing process and accelerate the hardening process, and c) the accelerators may not demonstrate toxicity. In an embodiment, the hardening accelerator may be supplied with the aqueous solution. For example, the aqueous solution may contain sodium phosphate dibasic ($Na_2HPO_4$) as a hardening accelerator. In an embodiment, the $Na_2HPO_4$ may be replaced, in the aqueous solution, by various alternatives, including monosodium phosphate ($NaH_2PO_4$), trisodium phosphate ($Na_3PO_4$), ammonium phosphate ($(NH_4)_3PO_4$), dipotassium phosphate ($K_2HPO_4$), sodium fluoride (NaF), potassium fluoride (KF), sodium acetate, potassium oxalate ($C_2K_2O_4$), sodium sulfate ($Na_2SO_4$), and sodium cacodylate ($C_2H_6AsNaO_2$). In addition, organic acids (glycolic, citric, tartaric, malonic, malic, maleic) may be used as a hardening accelerator. Finally, phosphate salts such as potassium and ammonium may be used as hardening accelerators.

In an embodiment, the herein disclosed scaffolds may be printed using a pre-mixed composition including the CPC slurry (CPC powder+polymer solution) and a hardening accelerator may be loaded into the syringe. The hardening times of the foregoing pre-mixture (CPC slurries+hardening accelerators) depend on the concentration of the hardening accelerators. The same hardening accelerators noted above may be used in the pre-mixture. Because the pre-mixture prints on the substrates quickly, the printing process can be finished before the pre-mixture hardens in the syringe.

In an embodiment, the TTCP particle size varies in a range from 1 μm to 17 μm and with different combination of DCPA particle size in a range from 1 μm to 5 μm. Slurries containing different particle sizes will print scaffolds with different mechanical properties and HA formation. Applicants printed HA scaffolds for two combinations including TTCP 17+DCPA 1 (larger syringe needle) and TTCP 5+DCPA 1 (smaller syringe needle). The particle size of DCPA should be smaller than that of TTCP or at least the same size, as shown in the table below.

TABLE 3

| TTCP (μm) | DCPA (μm) |
|---|---|
| 5-17 | 1-5 |
| 4 | 1-4 |
| 3 | 1-3 |
| 2 | 1, 2 |
| 1 | 1 |

In an embodiment, the CPC slurries may be printed with nozzles of 30, 80, 100, 160 μm, in addition to 210 μm, thereby achieving smaller (higher resolution) features within the scaffolds using smaller diameter nozzles.

Method of Synthesis, Assembly, and Production
Material Preparation Method
Preparation of Calcium Phosphate Cement Powder (Solid-Phase)

Calcium phosphate cement (CPC) was formulated by mixing 73% w/w tetracalcium phosphate (TTCP; $Ca_4(PO_4)_2O$) and 27% w/w the dicalcium phosphate anhydrous (DCPA; $CaHPO_4$). Preparation of TTCP and DCPA powders have been described before [31], [32]. The mixture of DCPA (J. T. Baker Chemical Co.) and $CaCO_3$ (J. T. Baker Chemical Co.) was heated at 1500° C. for six hours in a bottom loading furnace (KEITH, EHSK-12, CA). Afterward, the mixture was quenched in a desiccator at room temperature for two days. Initially, the solid was dry ground in a planetary ball mill (Retsch PM4, Brinkman, N.Y.) to obtain a median particle size of 17 μm (TTCP17). The TTCP17 was further ground by a planetary ball mill for 24 hours to obtain a median particle size of 5 μm (TTCP5). Nozzle clogging was reduced significantly using the smaller size of TTCP (TTCP5). Finally, the DCPA was ground by a planetary ball mill for 24 hours to obtain a median particle size of 1 μm (DCPA1).

Preparation of PVB/CPC Composite Solutions (Liquid Phase)

Figure 1:
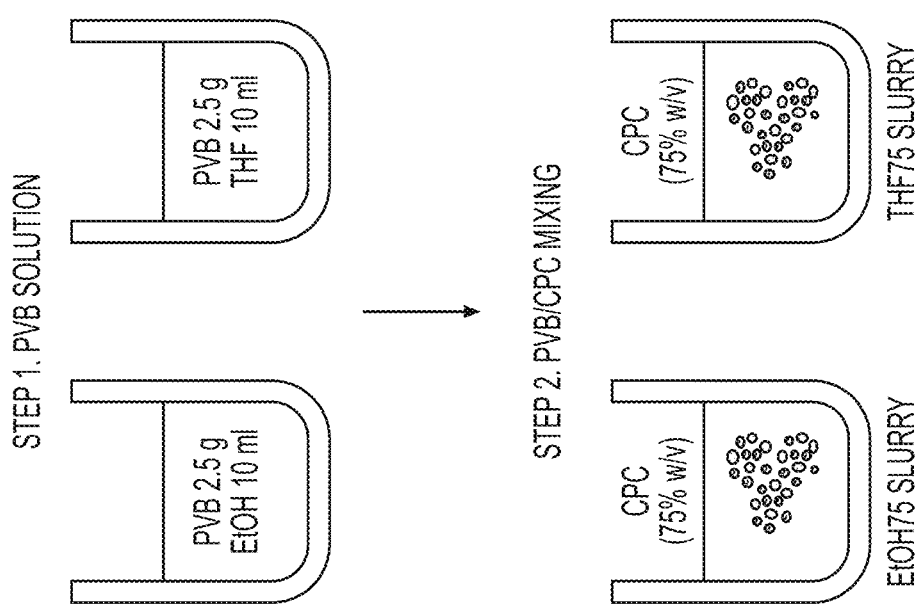
FIG. 1 is a schematic of a process for preparing polyvinyl butyral/calcium phosphate cement (PVB/CPC) slurries.
Figure 12B:
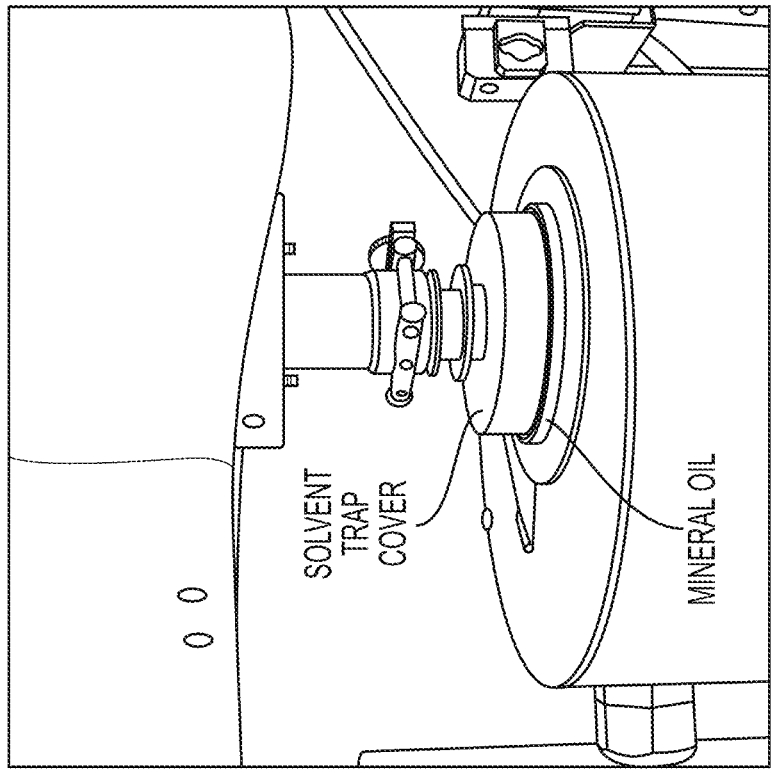
FIGS. 12A and 12B illustrate experimental setups for rheological measurements.
Figure 12A:
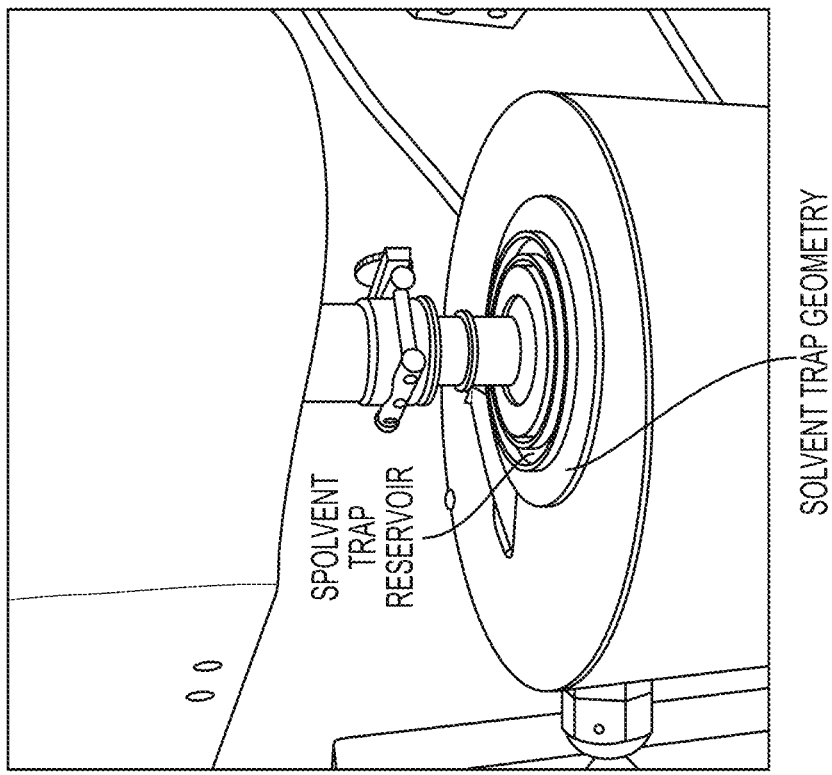

In this study, two different types of Poly(vinyl butyral) (PVB, Mw~60,000) (Scientific Polymer Inc., NY) solutions at a concentration of 25% w/v were prepared by (1) dissolving PVB in Ethanol (PVB/EtOH solution), and (2) dissolving PVB in Tetrahydrofuran (PVB/THF solution), each at 25° C. for 24 hours. Subsequently, the CPC powder (TTCP5+DCPA1) was added to the PVB/EtOH or PVB/THF solution in a weight ratio of 0.75 to 1, followed by magnetic stirring for 24 hours at 25° C. to create the PVB/EtOH/CPC slurry (EtOH75) and PVB/THF/CPC slurry (THF75), respectively. FIG. 1 illustrates this process schematically. To determine if the desired fabrication of 3D printed scaffolds was possible, and to ensure that a reproducible and fully-characterized biofabrication process could be defined, the printability of the bio-inks was tested. The viscosity of the slurries, EtOH75 and THF75, (see FIG. 2, which illustrates the viscosity (η) of different PVB/CPC slurries as a function of shear rate, with data expressed as the standard error of the mean (±SEM) for 4 measurements (N=4) by rheometer as shown in FIGS. 12A and 12B. In the absence of CPC powder, the viscosity of the PVB/EtOH solution (1.094±0.009 Pa s) was 1.8 times greater than that of the PVB/THF solution (0.602±0.004 Pa s). The PVB solutions showed Newtonian flow behavior below 100 1/s. However, in the presence of a CPC powder, the viscosities of the PVB/EtOH/CPC (11.012±0.322 Pa s) and the PVB/THF75/CPC (8.970±0.698 Pa s) slurries were higher (~10 times) than the PVB/EtOH solution and approximately 15 times higher than the PVB/THF solution, respectively. In addition, the CPC slurries exhibited shear thickening behavior at a low shear rate (<0.25 1/s), and then changed to shear thinning behavior over the remaining range of the shear rate.

Fabrication of PVB/HA Composite Scaffolds by 3D Printing

Figure 4:
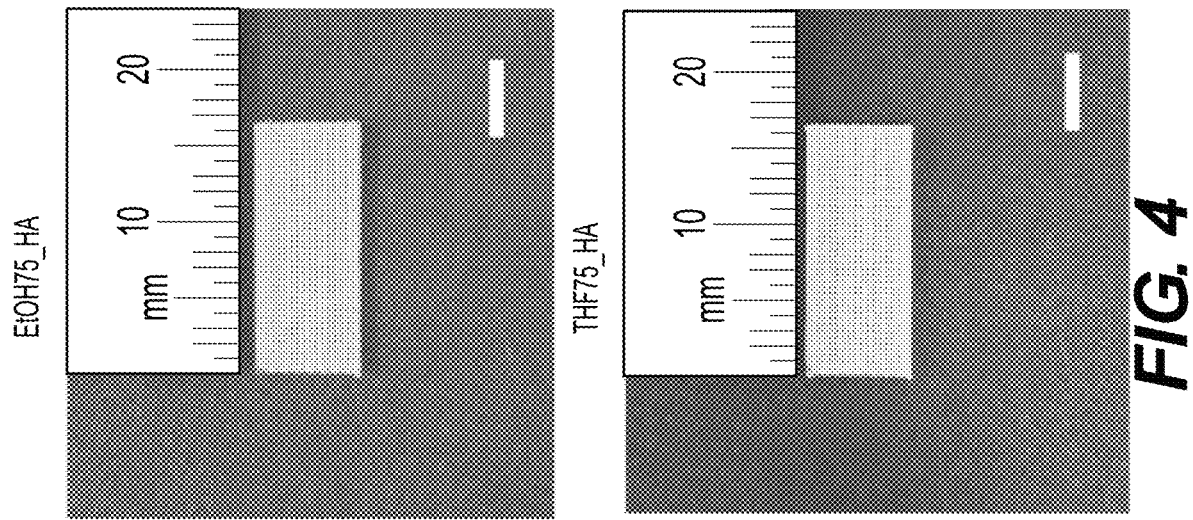
FIG. 4 presents representative images of PVB/HA scaffolds printed using a 210 μm diameter nozzle according to the schematic process of FIG. 3.
Figure 3:
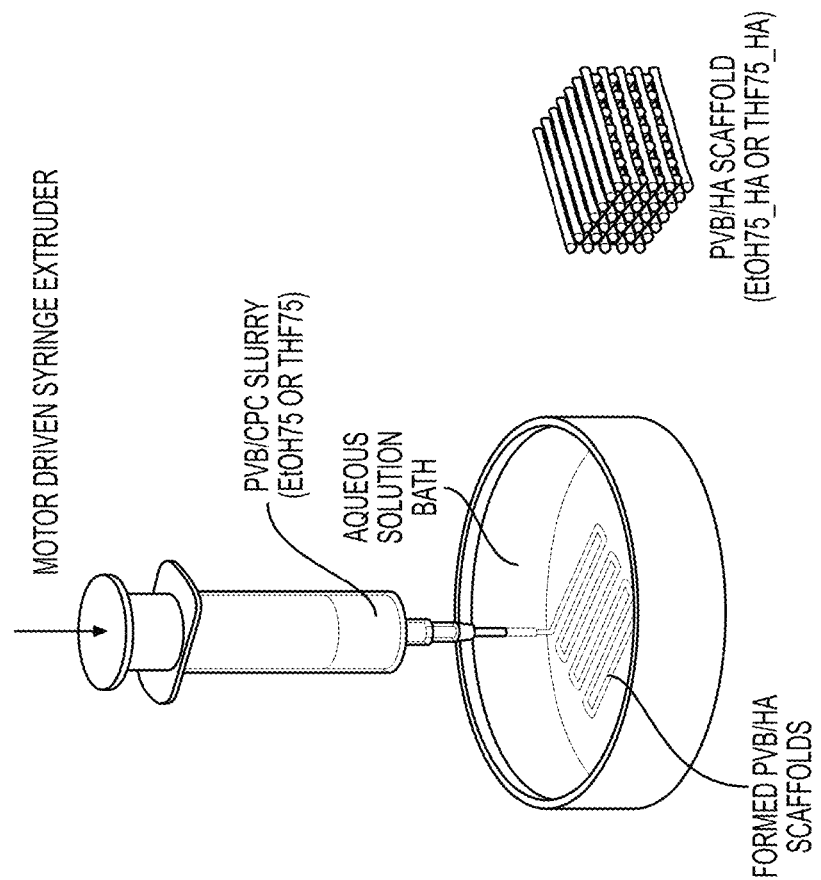
FIG. 3 is a schematic of a 3D printing used to produce PVB/HA scaffolds in an aqueous bath.

FIG. 3 is a schematic of an example 3D printing process used to produce Polyvinyl butyral (PVB)/Calcium Phosphate Cement (CPC) scaffolds in an aqueous bath. Referring to FIG. 3, a motor-driven syringe extruder with a nozzle diameter of 210 μm (27 gauge) of 3D bioprinter (Rokit Healthcare, INVIVO, South Korea) was filled first with the EtOH75 slurry and a printing process was executed. Next, the THF75 slurry was used. In both studies, the printing process was a constant speed of 5 mm/s in a 0.1M sodium phosphate dibasic ($Na_2HPO_4$) solution bath. The syringe and the aqueous bath were maintained at room temperature. In an embodiment, the depth of the aqueous bath was sufficient to completely submerge the scaffold to be printed. That is, the level of the aqueous bath was maintained higher than the planned height z of the printed scaffold. Other printing parameters were: filament gap of 210 μm, a layer thickness of 120 μm, and a lay-down pattern of 0°/90°. Hydroxyapatite (HA) formed upon reaction of the CPC component of the PVB/solvents/CPC slurries (EtOH75 or THF75) with $Na_2HPO_4$. Afterward, the final 3D printed scaffolds. PVB/solvent/HA (EtOH75_HA or THF75_HA), were dried at room temperature for 48 hours. FIG. 4 illustrates a 3D scaffold printed, using the apparatus of FIG. 3, showing a top view of the EtOH75_HA scaffold and the THF75_HA scaffold. The small bar in the bottom right corner of each image of FIG. 4 represents 5 mm.

Characterization of the 3D Printed Scaffolds, Testing and Results
In Situ HA Formation in 3D Printed Scaffolds
X-Ray Diffraction (XRD) Analysis Qualitative and quantitative information of the formation of HA in the scaffolds were obtained through X-ray diffraction (XRD) to reveal detailed information about chemical composition, crystallography, and structure of the scaffolds. XRD θ-2θ scans were collected on the PVB/HA scaffolds with dimensions of 17(L)×7(W)×1(H) mm at room temperature using a Philips Norelco diffractometer (vertical goniometer with automated scanning hardware) with Cu K-alpha radiation. The scanning range was from 10° to 60° with 0.03° 2θ steps and a 3 second count time at each step (FIG. 5).

Figure 5:
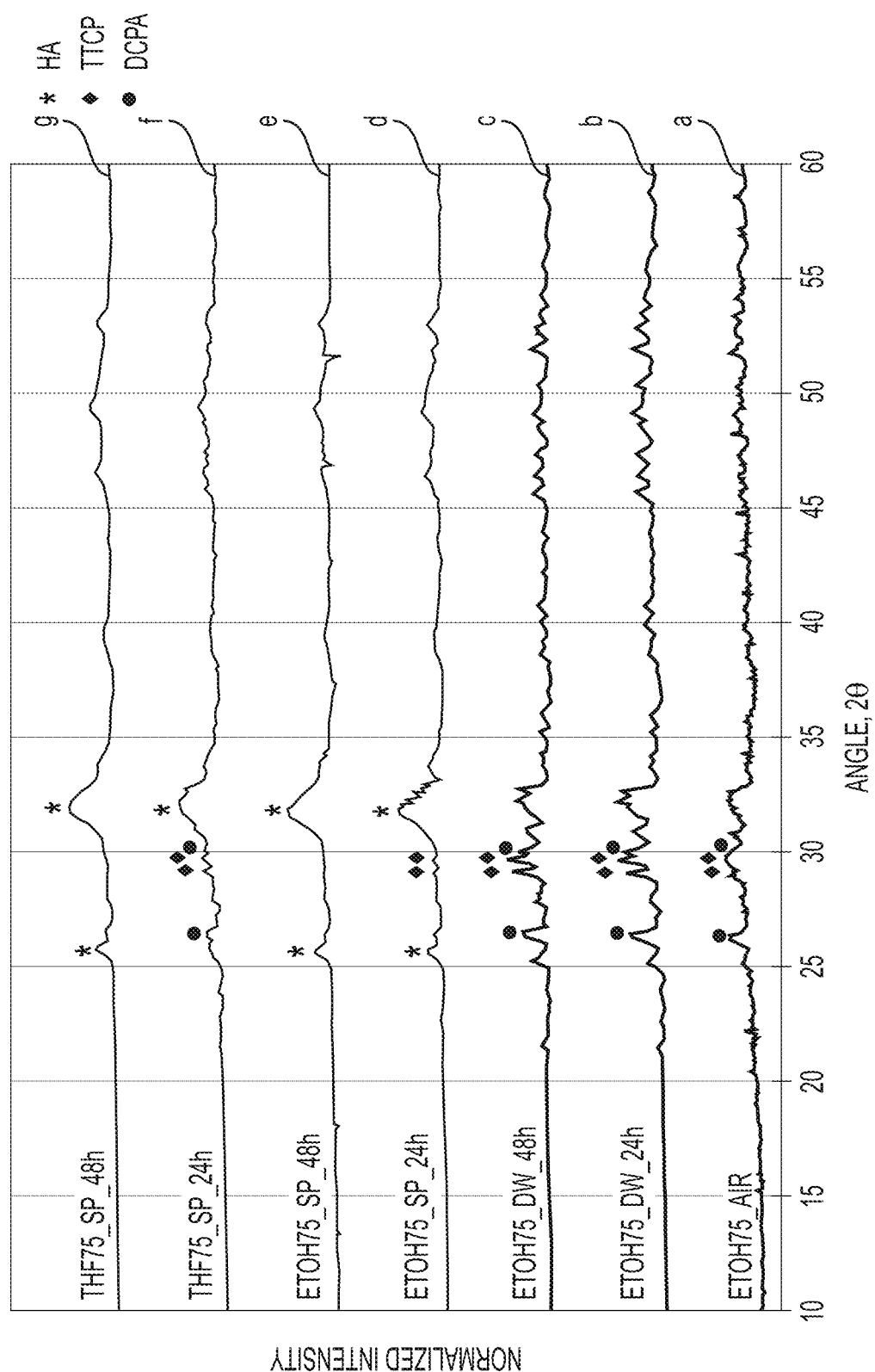
FIG. 5 presents a characterization of HA formation in a 3D printed scaffold.

The XRD data of FIG. 5 suggest that the presence of the $Na_2HPO_4$ bath during the 3D-printing is necessary or at least advantageous for in situ HA formation. The XRD diffraction data for the printed scaffolds, as shown in FIG. 5 validates that hypothesis. The data of FIG. 5 show the XRD spectrum of the PVB/CPC composite scaffold printed in air (curve a), printed in the presence of water (DW) for 24 hours (curve b) and 48 hours (curve c), and printed in the presence of $Na_2HPO_4$ (SP) for 24 hours (curves d and f) and 48 hours (curves e and g). Specifically, the EtOH75 slurry initially was printed in the air (without the aqueous solution), resulting in a scaffold containing only TTCP and DCPA (2θ) as shown by curve a of in FIG. 5. Next, the EtOH75 slurry was printed in presence of a water bath, resulting in the absence of HA formation independently of the immersion time (24 hours or 48 hours—see curves b and c of FIG. 5). Finally, in the presence of a $Na_2HPO_4$ aqueous solution during either EtOH75 or THF75 3-D printing process, HA formation was detected by XRD. The test results show that both EtOH75_HA and THF75_HA, when embedded for 48 hours in the $Na_2HPO_4$ solution, provided proper HA formation with no unreactive TTCP and DCPA (see FIG. 5, curves d, e, f, and g).

Scanning Electron Microscope Study

The detailed morphologies of the EtOH75_HA and THF75_HA were obtained by scanning electron microscope (SEM; JEOL, JSM-IT1500, MA) at an accelerating voltage of 10 kV. The SEM samples were vertically cut, mounted on aluminum sample studs, and coated with gold in the argon environment using a thin film sputter (Denton Vacuum, Desk V, NJ).

Figures 6A, 6B:
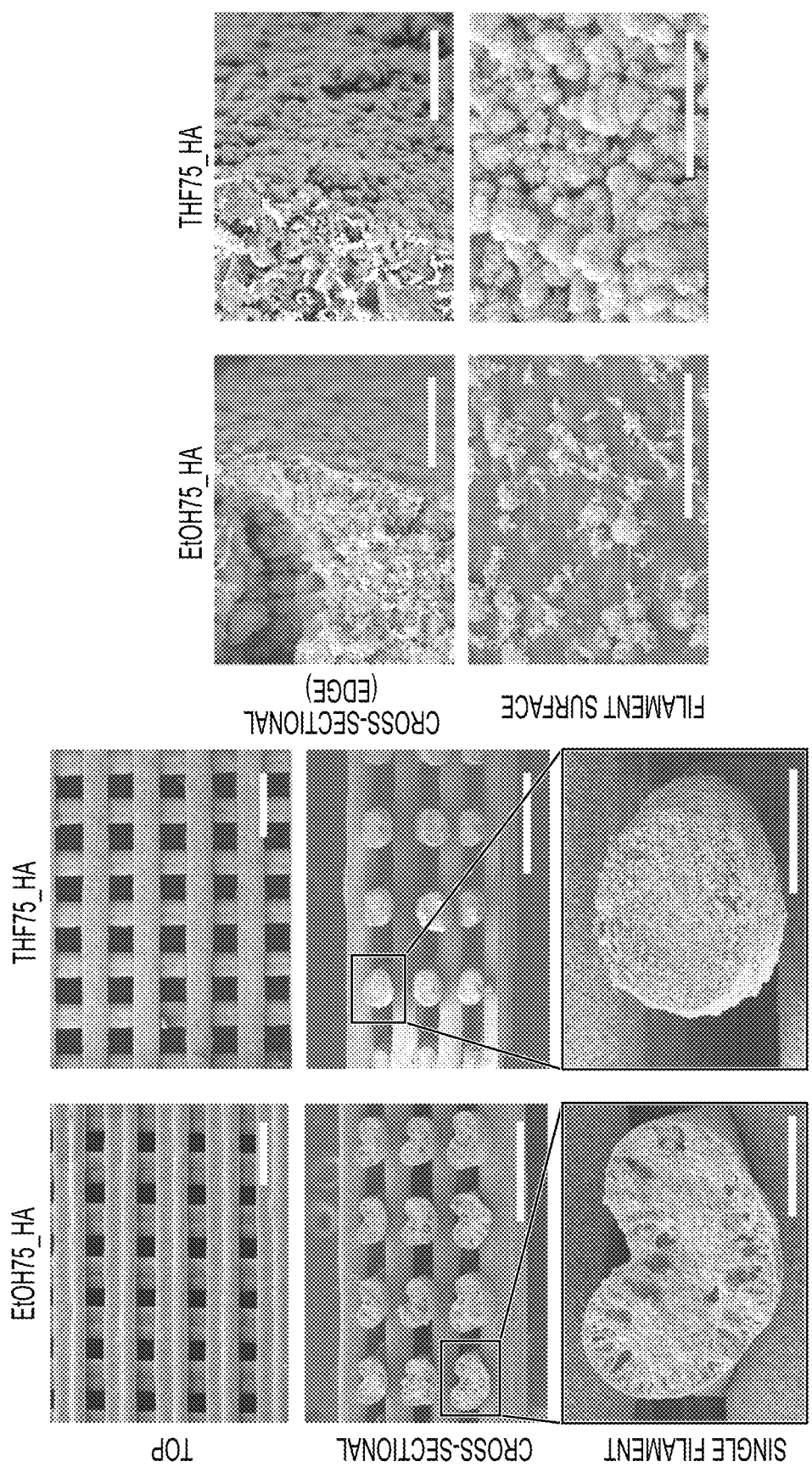
FIGS. 6A and 6B illustrate results of a scanning electron microscope (SEM) optical analysis of the PVB/HA scaffolds.

FIG. 6A provides a structural comparison of the two scaffolds, EtOH75_HA and THF75_HA. Scanning electron microscope (SEM) images from the "TOP" view (where the bar represents 500 µm), "CROSS-SECTIONAL" view (bar represents 500 µm) and "SINGLE FILAMENT" view (bar represents 100 µm) of the dried EtOH75_HA scaffold show different structures from those of the dried THF75_HA scaffold. As can be seen in the view marked "TOP," the EtOH75_HA printed filaments are wider and the gaps between filaments are narrower than those of the THF75_HA scaffold. As can be seen in FIGS. 6A and 6B SEM images from the top view and the cross-sectional view of the dried EtOH75_HA scaffolds show geometrical structures that differ from those of the THF75_HA scaffolds. Furthermore, the dimension (diameter) of EtOH75_HA printed filament (238.26±6.39 µm) was larger than the THF75_HA printed filament, which has a circular shape with dimension (164.98±6.85 µm) (the bar in FIG. 6B represents 10 µm).

Porosity of the Printed PVB/HA Composite Scaffolds

To further evaluate our porosity studies, applicants performed micro-computed tomography (micro-CT) for the two scaffolds. The porosity of the PVB/HA scaffolds was imaged by using micro-computed tomography (micro-CT) (Scanco Medical, µCT 40, PA). The specimens (17(L)×5(W)×3(H) mm) were placed on the PMMA sample holder (U40830) between the X-ray source and the CCD camera, such that the whole specimen was encompassed in the field of view. The exposure conditions were 180° rotations, 45 kVp, and 177 µA. The porosity from the scanned images was calculated by µCT evaluation program V6.5 with the range of the threshold values (Min. 352, and Max. 1000). Figures 7A and 7B present representative views of the two scaffold structures at micro-CT. FIG. 7C presents comparative porosity values for the two scaffolds. The THF75_HA scaffold showed higher porosity (60.60 %) compared to the EtOH75_HA scaffold (43.8 %).

Surface Area

FIG. 7D illustrates the disparity in surface area between the two scaffolds, with the EtOH75_HA showing an approximately 33% larger surface area than the THF75_HA scaffold.

Mechanical Properties

Scaffold geometry and microstructure are related to the mechanical properties of the scaffolds. To expand the herein disclosed studies and to further characterize the mechanical properties of the 3D printed scaffolds, applicants performed tensile strength and compressive strength tests, the results of which are shown, respectively, in FIGS. 8A-D, and 9A-9D.

Ultimate Tensile Strength (UTS) Measurement

The mechanical properties of EtOH75 and THF75 scaffolds with the dimension of 17(L)×7(W)×1(H) mm were measured using the universal tensile machine (Instru-Met Cop., Model 1122. NJ) with 1 kN load cell. The scaffolds were vertically mounted on two sample holders with adhesion glue. Load-deformation data were recorded at a cross-head speed of 1 mm/min, and then, Young's modulus, yield strength, and the ultimate tensile strength were calculated through the stress-strain curve.

Figure 8A:
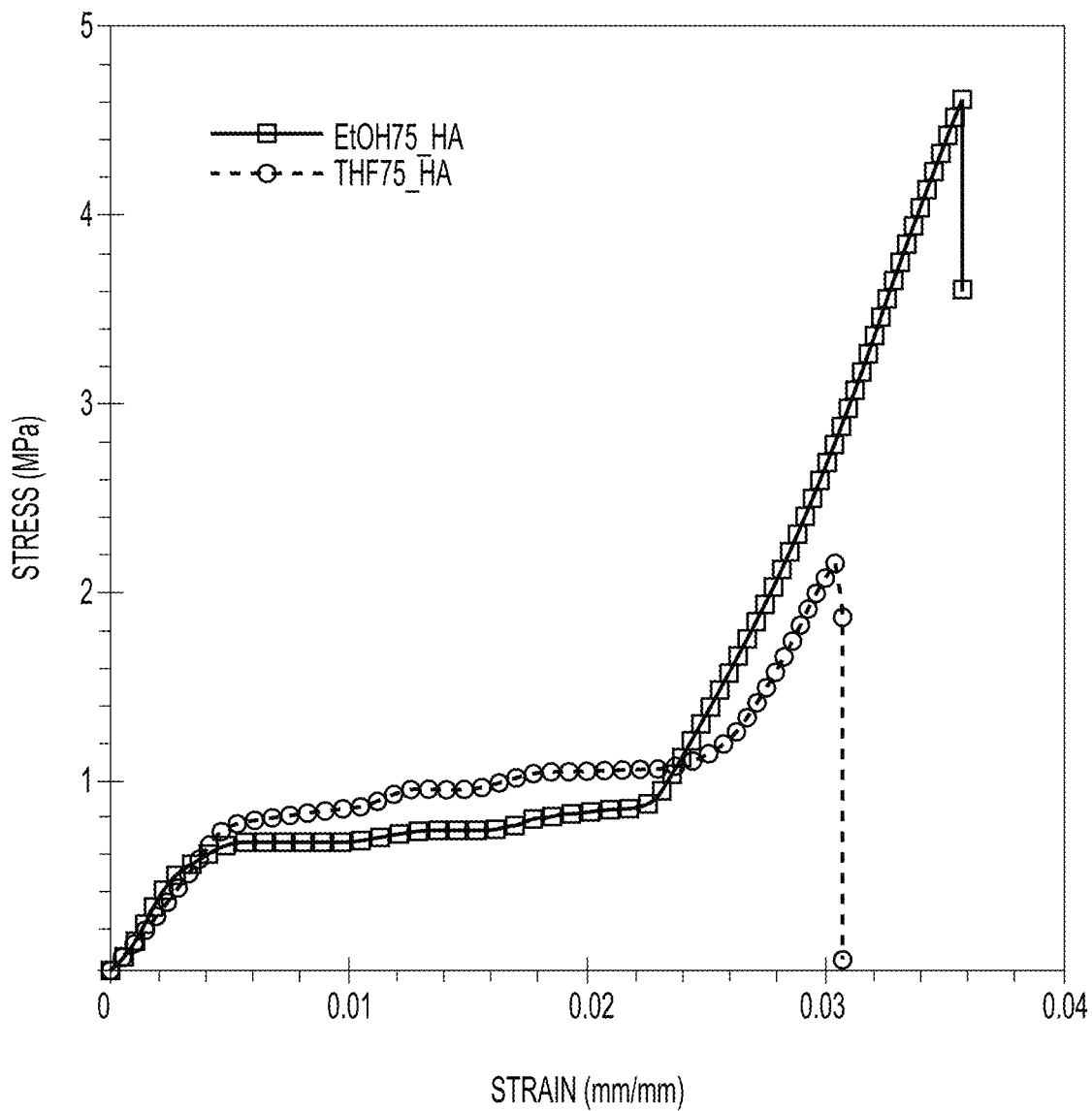

For the tensile strength test, the stress-strain curve for both scaffolds showed the initial elastic, plastic deformation, and rapid increase in stress (FIG. 8A). Although Young's modulus and yield strength of EtOH75_HA scaffolds were similar to the THF75_HA scaffold, the ultimate tensile strength (UTS) in EtOH75_HA scaffolds (3.72±0.97 MPa) was higher by 2-fold compared to THF75_HA scaffold (2.0±0.14 MPa) (FIGS. 8B, C, D).

Compressive Strength Measurement

Figure 9A:
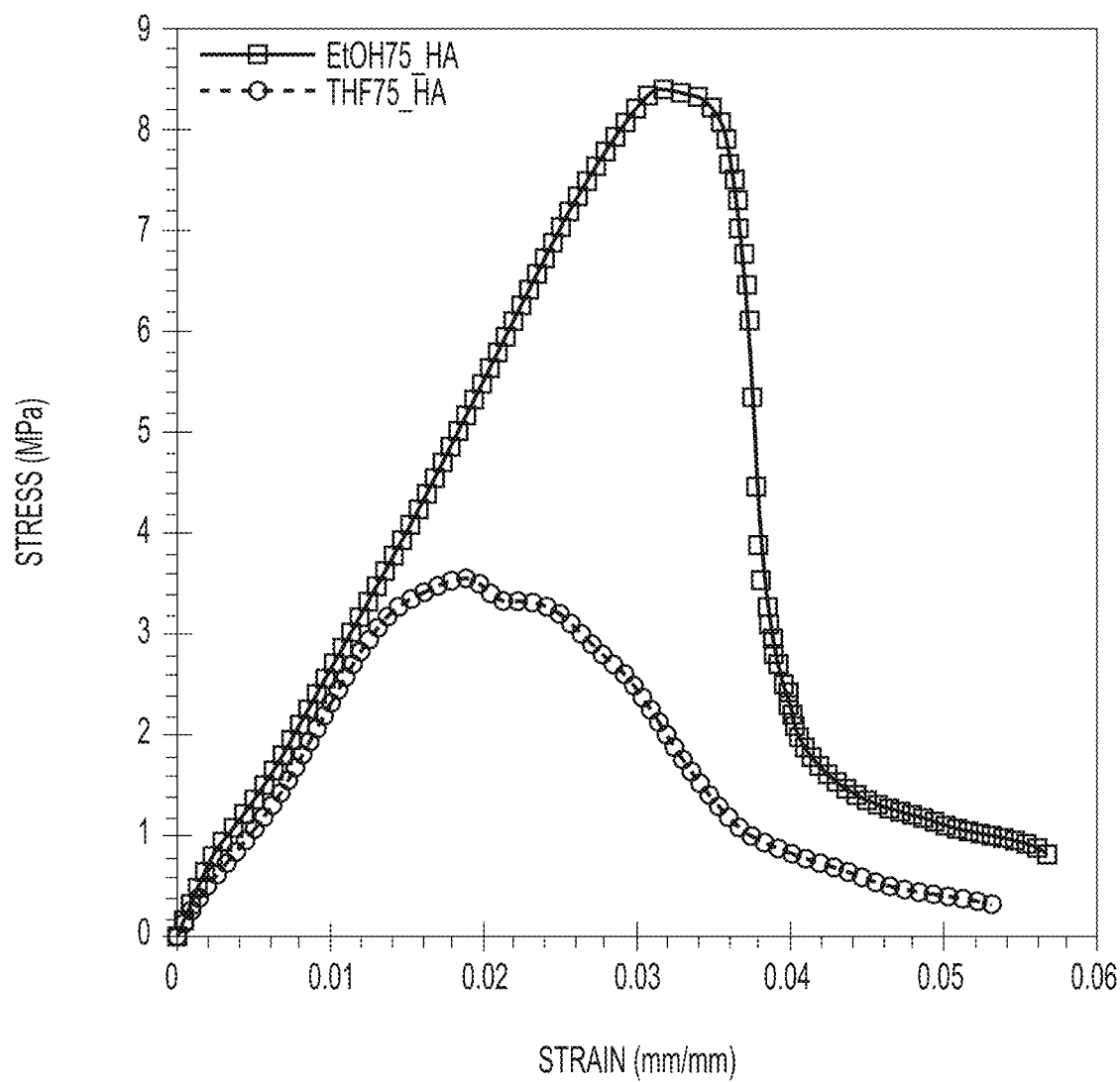

The compressive strength tests show results similar to the tensile strength tests. See FIG. 9A. The compressive modulus and compressive yield strength of EtOH75_HA and THF75_HA show similar values, but ultimate compressive strength in EtOH75_HA scaffolds (7.74±1.13 MPa) was higher by 3.4-fold than that of THF75_HA scaffold (2.28±1.22 MPa) (FIGS. 9 B, C, D). The porosity tests and strength measurements, taken together, illustrate that the microstructure of the THF75_HA scaffold has a higher porosity and a more brittle behavior than the EtOH75_HA scaffold.

Osteoconductivity of the 3D Printed Scaffolds

The scaffolds were assayed for osteogenesis by staining for Alkaline Phosphatase with Leukocyte Alkaline Phosphatase kit (Sigma), for protein-associated calcification with Alizarin Red S (AR), and for mineral deposition with Silver Nitrate solution (Von Kossa: VK). The scaffolds were fixed in 4% paraformaldehyde (PFA; Sigma) for 20 minutes at 37° C., washed twice in PBS, permeabilized with 0.1 % (v/v) Triton ×100 in PBS for 20 minutes at RT, and treated with blocking solution (0.01% (v/v) Triton ×100, 5% (w/v) goat serum (Sigma) in PBS) overnight at 4° C. Next day, DAPI (1:1000, Sigma), and Alexa Fluor 647 Phalloidin (1:200, Thermo Fisher) were added and incubated overnight at 4° C. Finally, the cells were stained for cell viability/cytotoxicity by using LIVE/DEAD™ Viability/Cytotoxicity Kit (ThermoFisher). The scaffolds were imaged using a confocal microscope (LSM 800, Carl Zeiss), and image analysis made by Image J by performing a maximum intensity z projection and merging the channels.

Figure 10C:
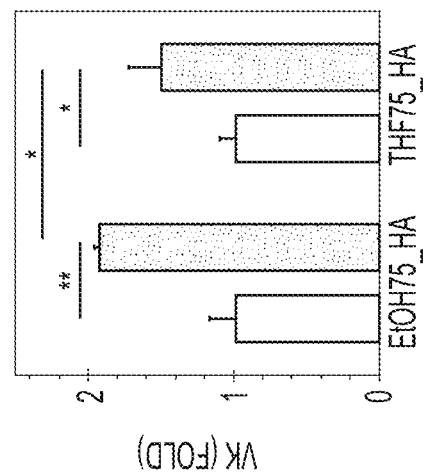
FIGS. 10A-10C illustrate results of osteoconductivity measurements for 3D printed scaffolds by staining.
Figure 10B:
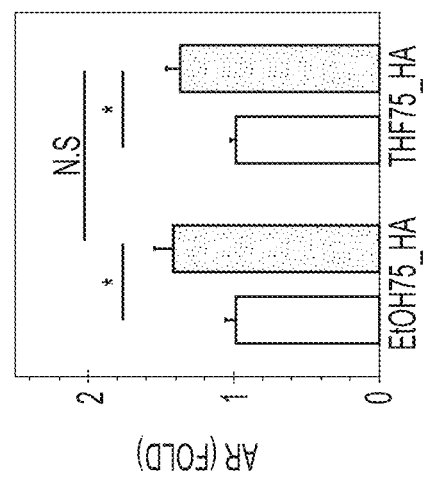
Figure 10A:
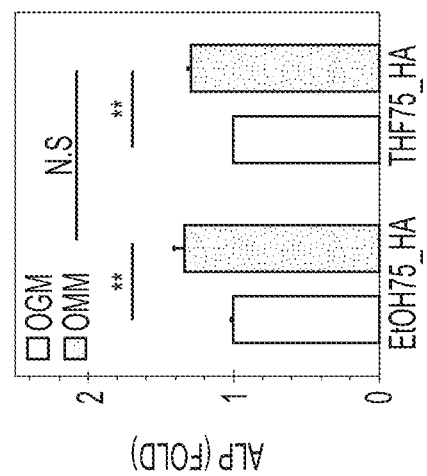
Figure 11A:
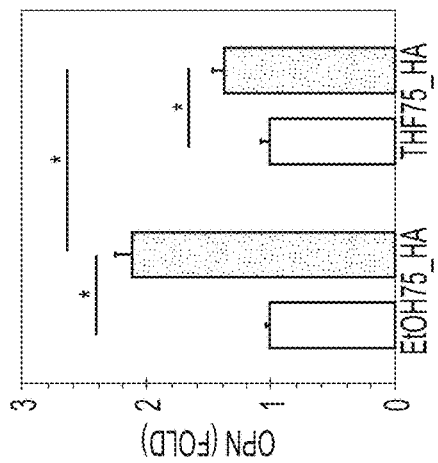
FIGS. 11A-11F illustrate regulation of genes involved in osteoblast differentiation and mineralization.
Figure 11B:
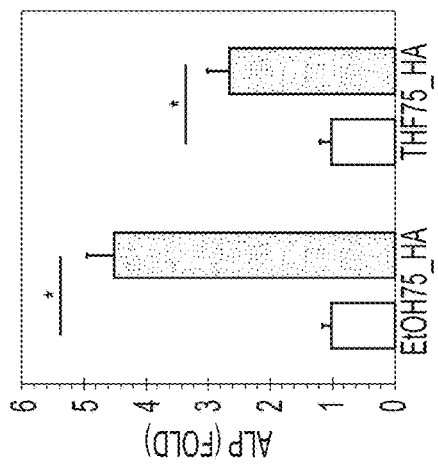
Figure 11C:
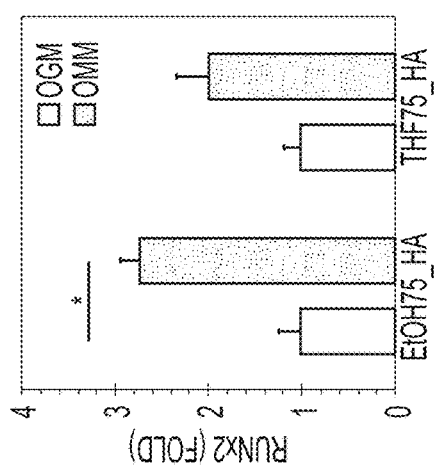
Figure 11D:
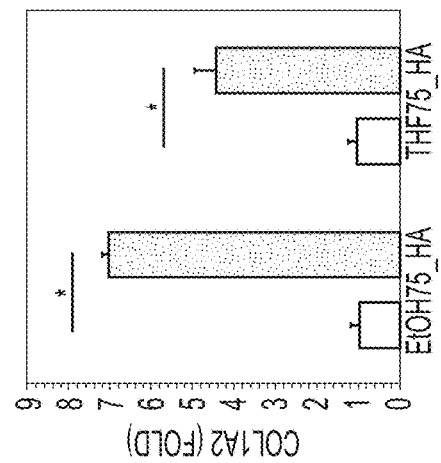
Figure 11E:
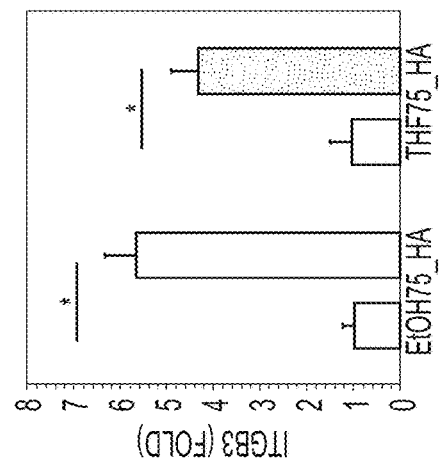
Figure 11F:
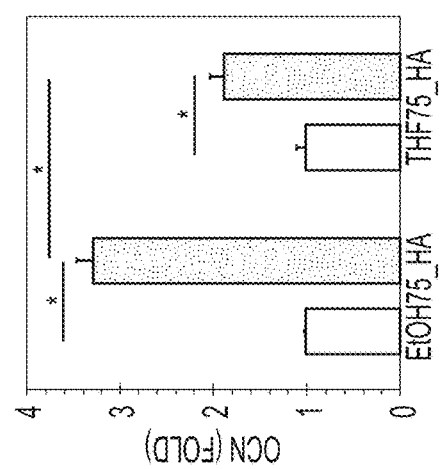

After the scaffold characterization, cytocompatibility and osteoconductivity of the 3D printed scaffolds were tested. Initially, human osteoblasts (OBSTs) attached and spread on the 3D printed scaffolds. To test the mineralization and osteoconductivity potential of the cells on the 3D printed scaffolds. Alkaline Phosphate (ALP), Alizarin Red (AR), and Von Kossa (VK) staining were performed. The cells cultured on the EtOH75_HA scaffold under mineralization conditions showed higher mineralization (~2-fold) compared to the THF75_HA scaffold as shown in FIGS. 10A-C.

Cell Culture

Primary Human OBSTs (Promocell) were cultured in Osteoblast Growth Medium Supplement Mix (OGM) (Promocell). All experiments were performed with HOBs at passage 4 to 5. Finally, for differentiation assays, the HOBs were plated on 3D printed scaffolds (3(L)×3(W)×0.5(H) mm) at 0.5 million/ml density. All scaffolds samples were sterilized with 70% Ethanol and treated ultraviolet (UV) irradiation for 12 hours. The next day, the cells were exposed to Osteoblast Mineralization Medium (OMM) (Promocell) for 10 days in a humidified incubator in an atmosphere containing 5% v/v $CO_2$ at 37° C.

Figure 13:
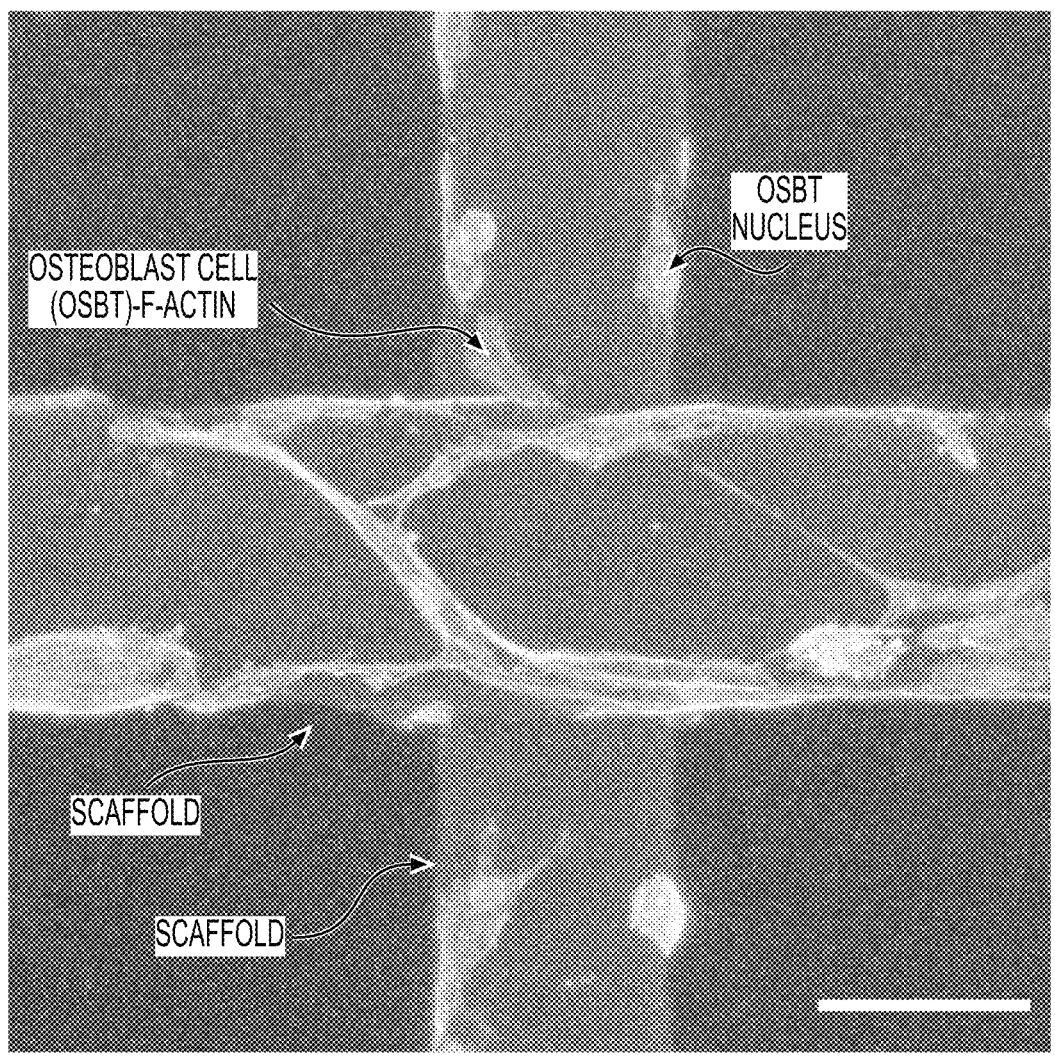
FIG. 13 illustrates osteoblast attachment and spread on a 3D printed scaffold based on immunostaining for F-actin (phalloidin) and DAPI (nuclei)
Figure 14B:
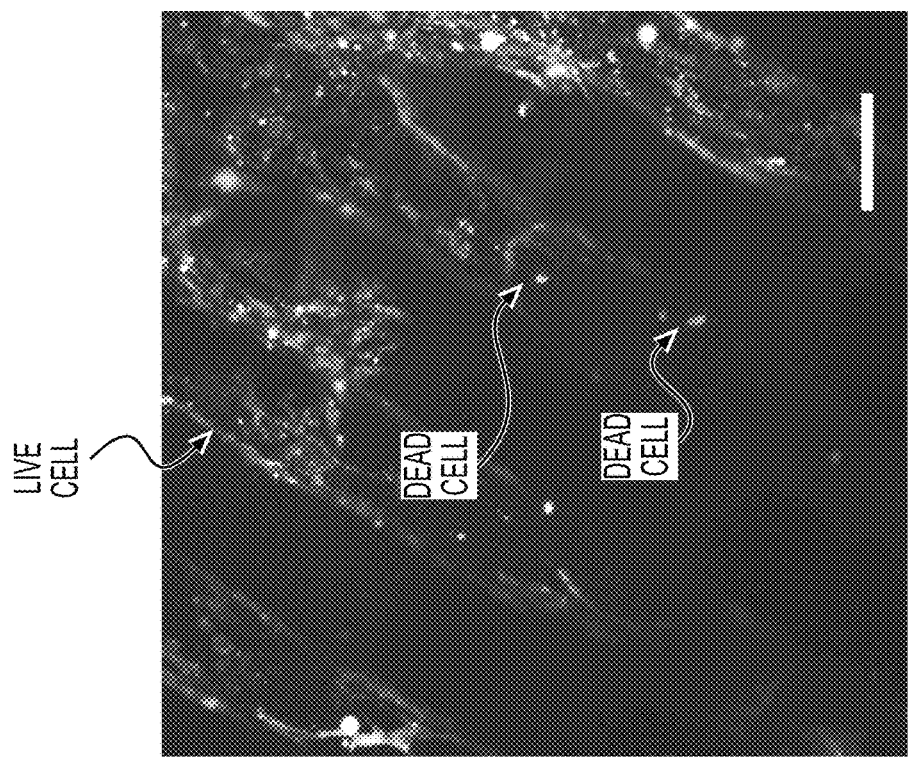
FIGS. 14A and 14B illustrate the results of Live/Dead assays on 3D printed scaffolds.
Figure 14A:
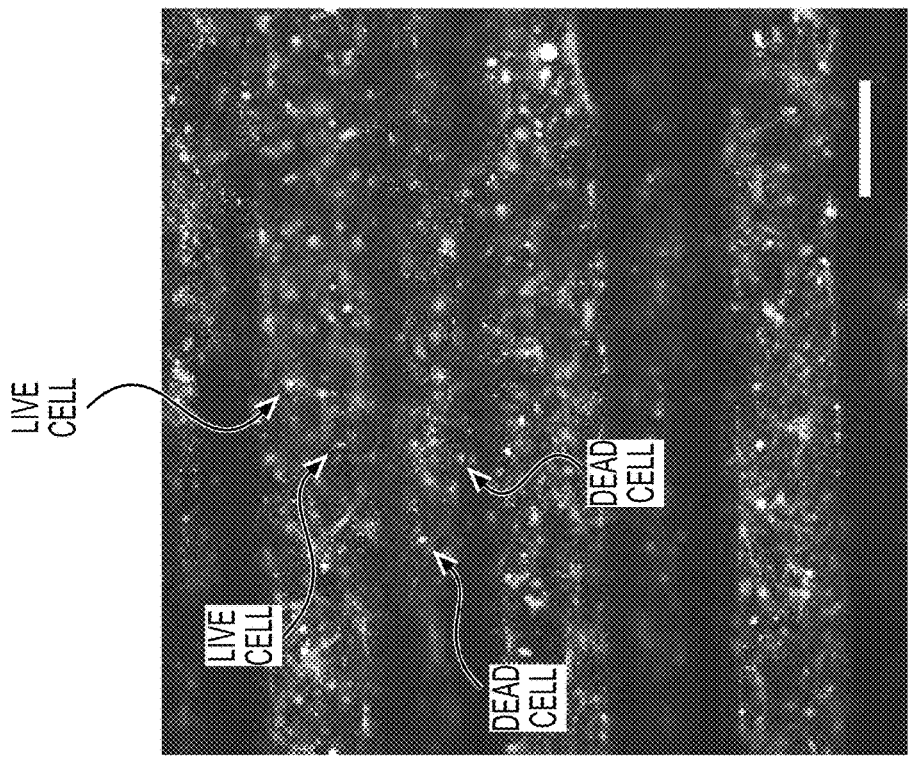

Initially, applicants confirmed the OBSTs attachment and spread on the 3D printed scaffold by F-actin (phalloidin) staining (FIG. 13). The cells were spread on the printed filaments as indicated in FIG. 13. The OSBT were stained for F-actin (phalloidin) and DAPI for the nuclei (OSBT nuclei). After 14 days OGM culturing the cells, their viability was tested on the Live/Dead assay (FIGS. 14A and 14B). Next, applicants tested the mineralization and osteoconductivity potential of the cells on the 3D printed scaffolds by Alkaline Phosphate (ALP), Alzarin Red (AR), and Von Kossa (VK) staining. OSBTs on EtOH75_HA and THF75_HA scaffolds were cultured in OMM conditions for 14 days demonstrated a 1.5-fold increase compared to OGM conditions based on ALP (FIG. 10A). Similarly, cells cultured under OMM conditions in both scaffolds showed 1.5-fold increase based on AR staining (FIG. 10B). Finally, our VK study showed that the cells cultured in OMM conditions exhibited 2-fold and 1.5-fold increase in EtOH75_HA and THF75_HA, respectively. Additionally, the cells cultured on the EtOH75_HA scaffold showed higher mineralization capacity (~2-fold) compared to the THF75_HA scaffold (FIG. 10C). To further evaluate the molecular mechanisms associated with the bone regeneration activity of OBSTs on EtOH75_HA and THF75_HA scaffolds, we analyzed their capacity to regulate the genes involved in osteoblast differentiation and mineralization. The expression of the typical OB-specific genes, including runt-related transcription factor 2 (Runx2), alkaline phosphatase (ALP), osteopontin (OPN), osteocalcin (OCN), integrin β3 (ITGB3), and collagen type I alpha 2 (COL1A2), was determined. Quantitative real-time polymerase chain reaction (qRT-PCR) analysis revealed that the expression of RunX2, ALP, OPN, OCN, ITGB3, and COL1A2 increased in OMM cultures compared to those in OGM cultures (FIGS. 11A-11F). These results clearly demonstrated that OB differentiation gene expression was dramatically up-regulated in OMM cultures of OBST seeded scaffolds.

Statistical Analysis

Statistical analysis of the quantitative data was conducted by one-way Analysis of Variance (ANOVA) using SPSS software. The p-values of less than 0.05 were considered as significant.

Biocompatibility

The 3D-printed scaffolds demonstrated osteoconductivity based on the ALP, AR and VK staining and relative mRNA level expression of key osteogenic markers such as COL1A1, ALP. Applicants expect the 3D-printed scaffolds may be used to support growth of different cell types or combination of sell types, including:

Mesenchymal stem cells (MSCs), which are differentiating to osteoblasts;
Induced pluripotent stem cells (IPSCs), which are differentiating to osteoblasts;
Osteoids;
Osteoclasts precursor cells;
Peripheral blood mononuclear cell (PBMC), which are differentiating to osteoclasts;
Endothelial progenitor cell (EPC);
Endothelial cells;
Macrophages; and
Neutrophils.

Additionally, these cells may be encapsulated as necessary and then mixed with CPC/polymer in the slurry. The advantage is that the cell-containing slurries may be printed on specific locations in the CPC-scaffolds, thereby offering direct integration of the cells into the scaffold, avoiding a 14-day culture on the scaffolds, and faster osteointegration and repair with the native tissue.

FIG. 15 illustrates an example of a composition-controlled 3D printing system. In FIG. 15, a composition-controlled 3D printing system 100 includes a liquid composition sub-system, a liquid flow control sub-system, an aqueous bath sub-system, and a processor sub-system. The above sub-systems cooperate to produce 3D, composition-controlled product 200, for example, a biocompatible polymer/hydroxyapatite composite scaffold for bone repair. More specifically, the system 100 includes computer 110 which may execute machine instructions to control specific components of the system 100, specifically liquid flow control sub-system 120 and scanning stage 140. Other components of the system 100 include reservoir 130 and aqueous bath system 150. The reservoir contains a PVB/CPC slurry. The slurry is formulated by mixing a solid phase composition and a liquid phase composition. The liquid phase composition is prepared by mixing a polymer (e.g., PVB) with a solvent (e.g., EtOH or THF) to dissolve the PVB. The slurry may be prepared in advance of the printing and stored. Alternately, the slurry may be prepared as a first step in the printing process. The aqueous bath 150 contains a $Na_2HPO_4$ composition. Upon printing, the CPC components of the slurry react with $Na_2HPO_4$, and the solvents evaporate, resulting in in situ polymer/HA formation and the fabrication of the desired composite scaffold. The flow control sub-system 120 controls a motor (not shown) to operate extruding syringe 122 to control the flow of reactant compositions from reservoir 130 into discharge component 124 and the rate of deposition of the slurry through nozzle 128. The nozzle 128 deposits the slurry onto the scanning stage 140. The scanning stage 140 is immersed in aqueous bath sub-system 150. The computer 110 further controls three-dimensional motion of the nozzle 128 over a substrate placed on, or integral to, the scanning stage 140.

In an embodiment, the syringe 122 discharge component 124 and nozzle 128 may be replaced by a multiple syringe-discharge component-nozzle structure, which in turn may be coupled to multiple reservoirs 130. With this embodiment, the 3D-printed scaffold may be printed with slurries having differing compositions. In addition, the structure may permit deposition of cell-material on specific portions of the printing scaffold so as to achieve a desired non-uniform cell distribution.

References Cited Herein:

[1] A. Ramasamy, A. M. Hill, S. Masouros, I. Gibb, A. M. J. Bull, J. C. Clasper. Blast-related fracture patterns: A forensic biomechanical approach, J. R. Soc. Interface. 8 (2011) 689-698. https://doi.org/10.1098/rsif.2010.0476.

[2] A. Gupta, N. Kukkar, K. Sharif, B. J. Main, C. E. Albers, S. F. El-Amin, Bone graft substitutes for spine fusion: A brief review, World J. Orthop. 6 (2015) 449-456. https://doi.org/10.5312/wjo.v6.i6.449.

[3] J. Wolff, H. Agata, G. K. Sándor, S. Haimi, Peri-Implant Tissue Findings in Bone Grafted Oral Cancer Patients Compared to non Bone Grafted Patients without Oral Cancer, J. Oral Maxillofac. Res. 2 (2011) 1-8. https://doi.org/10.5037/jomr.2011.2402.

[4] P. D. Millikan, V. Karas, S. S. Wellman, Treatment of osteonecrosis of the femoral head with vascularized bone grafting, Curr. Rev. Musculoskelet. Med. 8 (2015) 252-259. https://doi.org/10.1007/s12178-015-9285-8.

[5] J. A. Goulet, L. E. Senunas, G. L. DeSilva, M. L. V. H. Greenfield, Autogenous iliac crest bone graft: Complications and functional assessment, Clin. Orthop. Relat. Res. (1997) 76-81. https://doi.org/10.1097/00003086-199706000-00011.

[6] A. S. Greenwald, S. D. Boden, V. M. Goldberg, Y. Khan, C. T. Laurencin, R. N. Rosier, Bone-Graft Substitutes: Facts, Fictions, and Applications, J. Bone Jt. Surgery- American Vol. 83 (2001) 98-103. https://doi.org/10.2106/00004623-200100022-00007.

[7] P. Baldwin, D. J. Li, D. A. Auston, H. S. Mir, R. S. Yoon, K. J. Koval, Autograft, Allograft, and Bone Graft Substitutes, J. Orthop. Trauma. 33 (2019) 203-213. https://doi.org/10.1097/BOT.0000000000001420.

[8] B. Grigoryan, S. J. Paulsen, D. C. Corbett, D. W. Sazer, C. L. Fortin, A. J. Zaita, P. T. Greenfield, N. J. Calafat, J. P. Gounley, A. H. Ta, F. Johansson, A. Randles, J. E. Rosenkrantz, J. D. Louis-rosenberg, P. A. Galie, K. R. Stevens, J. S. Miller, Multivascular networks and functional intravascular topologies within biocompatible hydrogels, 464 (2019) 458-464.

[9] J. S. Miller, K. R. Stevens, M. T. Yang, B. M. Baker, D.-H. T. Nguyen, D. M. Cohen, E. Toro, A. A. Chen, P. A. Galie, X. Yu, R. Chaturvedi, S. N. Bhatia, C. S. Chen, Rapid casting of patterned vascular networks for perfusable engineered three-dimensional tissues, Nat. Mater. 11 (2012) 768-774. https://doi.org/10.1038/nmat3357.

[10] N. Y. C. Lin, K. A. Homan, S. S. Robinson, D. B. Kolesky, N. Duarte, A. Moisan, J. A. Lewis, Renal reabsorption in 3D vascularized proximal tubule models. Proc. Natl. Acad. Sci. U. S. A. 116 (2019) 5399-5404. https://doi.org/10.1073/pnas.1815208116.

[11] D. B Kolesky, K. A. Homan, M. A. Skylar-Scott, J. A. Lewis, Three-dimensional bioprinting of thick vascularized tissues, Proc. Natl. Acad. Sci. U. S. A. 113 (2016) 3179-3184. https://doi.org/10.1073/pnas.1521342113.

[12] N. A. Chartrain, C. B. Williams, A. R. Whittington, A review on fabricating tissue scaffolds using vat photopolymerization, Acta Biomater. 74 (2018) 90-111. https://doi.org/10.1016/j.actbio.2018.05.010.

[13] X. P. Tan, Y. J. Tan, C. S. L. Chow, S. B. Tor, W. Y. Yeong, Metallic powder-bed based 3D printing of cellular scaffolds for orthopaedic implants: A state-of-the-art review on manufacturing, topological design, mechanical properties and biocompatibility, Mater. Sci. Eng. C. 76 (2017) 1328-1343. https://doi.org/10.1016/j.msec.2017.02.094.

[14] H.-T. Liao, M.-Y. Lee, W.-W. Tsai, H.-C. Wang, W.-C. Lu, Osteogenesis of adipose-derived stem cells on polycaprolactone-β-tricalcium phosphate scaffold fabricated via selective laser sintering and surface coating with collagen type I, J. Tissue Eng. Regen. Med. 10(2016) E337-E353. https://doi.org/10.1002/term.1811.

[15] J.-H. Shim, S. E. Kim, J. Y. Park, J. Kundu, S. W. Kim, S. S. Kang, D.-W. Cho, Three-Dimensional Printing of rhBMP-2-Loaded Scaffolds with Long-Term Delivery for Enhanced Bone Regeneration in a Rabbit Diaphyseal Defect, Tissue Eng. Part A. 20 (2014) 1980-1992. https://doi.org/10.1089/ten.tea.2013.0513.

[16] R. Trombetta, J. A Inzana, E. M. Schwarz, S. L. Kates, H. A. Awad, 3D Printing of Calcium Phosphate Ceramics for Bone Tissue Engineering and Drug Delivery. Ann. Biomed. Eng. 45 (2017) 23-44. https://doi.org/10.1007/s10439-016-1678-3.

[17] X. Li, Y. Yuan, L. Liu, Y.-S. Leung, Y. Chen, Y. Guo, Y. Chai, Y. Chen, 3D printing of hydroxyapatite/tricalcium phosphate scaffold with hierarchical porous structure for bone regeneration, Bio-Design Manuf. 3 (2020) 15-29. https://doi.org/10.1007/s42242-019-00056-5.

[18] B. Leukers, H. Gülkan, S. H. Irsen, S. Milz, C. Tille, M. Schieker, H. Seitz, Hydroxyapatite scaffolds for bone tissue engineering made by 3D printing, J. Mater. Sci. Mater. Med. 16 (2005) 1121-1124. https://doi.org/10.1007/s10856-005-4716-5.

[19] F. Fahimipour, M. Rasoulianboroujeni, E. Dashtimoghadam, K. Khoshroo, M. Tahriri, F. Bastami, D. Lobner, L. Tayebi, 3D printed TCP-based scaffold incorporating VEGF-loaded PLGA microspheres for craniofacial tissue engineering, Dent. Mater. 33 (2017) 1205-1216. https://doi.org/10.1016/j.dental.2017.06.016.

[20] A. Bruyas, F. Lou, A. M. Stahl, M. Gardner, W. Maloney, S. Goodman, Y. P. Yang, Systematic characterization of 3D-printed PCL/β-TCP scaffolds for biomedical devices and bone tissue engineering: Influence of composition and porosity, J. Mater. Res. 33 (2018) 1948-1959. https://doi.org/10.1557/jmr.2018.112.

[21] Y. Wen, S. Xun, M. Haoye, S. Baichuan, C. Peng, L. Xuejian, Z. Kaihong, Y. Xuan, P. Jiang, L. Shibi, 3D printed porous ceramic scaffolds for bone tissue engineering: a review, Biomater. Sci. 5(2017) 1690-1698. https://doi.org/10.1039/C7BM00315C.

[22] M. Touri, F. Moztarzadeh, N. A. A. Osman, M. M. Dehghan, M. Mozafari, 3D-printed biphasic calcium phosphate scaffolds coated with an oxygen generating system for enhancing engineered tissue survival, Mater. Sci. Eng. C. 84 (2018) 236-242. https://doi.org/10.1016/j.msec.2017.11.037.

[23] L. Dong, S. J. Wang, X. R. Zhao, Y. F Zhu, J. K. Yu, 3D-printed poly (ε-caprolactone) scaffold integrated with cell-laden chitosan hydrogels for bone tissue engineering, Sci. Rep. 7 (2017) 4-12. https://doi.org/10.1038/s41598-017-13838-7.

[24] R. Donate, Z. Ortega, L. Wang, V. Ribeiro, D. Pestana, M. Joaquim, R. L. Reis, Comparison between calcium carbonate and β-tricalcium phosphate as additives of 3D printed scaffolds with polylactic acid matrix, J. Tissue Eng. Regen. Med. (2019) 0-2. https://doi.org/10.1002/term.2990.

[25] C. Qian, F. Zhang, J. Sun, Fabrication of Ti/HA composite and functionally graded implant by three-dimensional printing, Biomed. Mater. Eng. 25 (2015) 127-136. https://doi.org/10.3233/BME-151263.

[26] J. Liu, J. Ruan, L. Chang, H. Yang, W. Ruan, Porous Nb-Ti-Ta alloy scaffolds for bone tissue engineering: Fabrication, mechanical properties and in vitro/vivo biocompatibility, Mater. Sci. Eng. C. 78 (2017) 503-512. https://doi.org/10.1016/j.msec.2017.04.088.

[27] J. Wieding, A. Jonitz, R. Bader, The effect of structural design on mechanical properties and cellular response of additive manufactured titanium scaffolds, Materials (Basel). 5 (2012) 1336-1347. https://doi.org/10.3390/ma5081336.

[28] E. De Giglio, M. A. Bonifacio, A. M. Ferreira, S. Cometa, Z. Y. Ti, A. Stanzione, K. Dalgarno, P. Gentile, Multi-compartment scaffold fabricated via 3D-printing as in vitro co-culture osteogenic model, Sci. Rep.8 (2018) 15130. https://doi.org/10.1038/s41598-018-33472-1.

[29] S. M. Bittner, B. T. Smith, L. Diaz-Gomez, C. D. Hudgins, A. J. Melchiorri, D. W. Scott, J. P. Fisher, A. G. Mikos, Fabrication and mechanical characterization of 3D printed vertical uniform and gradient scaffolds for bone and osteochondral tissue engineering, Acta Biomater. 90 (2019) 37-48. https://doi.org/10.1016/j.actbio.2019.03.041.

[30] Y. Cao, L. Xiao, Y. Cao, A. Nanda, C. Xu, Q. Ye, 3D printed β-TCP scaffold with sphingosine 1-phosphate coating promotes osteogenesis and inhibits inflammation, Biochem. Biophys. Res. Commun. 512 (2019) 889-895. https://doi.org/10.1016/j.bbrc.2019.03.132.

[31] K. Ishikawa, S. Takagi, L. C. Chow, K. Suzuki, Reaction of calcium phosphate cements with different amounts of tetracalcium phosphate and dicalcium phosphate anhydrous, J. Biomed. Mater. Res. 46 (1999) 504-510. https://doi.org/10.1002/(SICI)1097-4636(19990915)46:4<504::AID-JBM8>3.0.CO;2-H.

[32] Y. Shimada, T. Medical, L. C. Chow, S. Takagi, J. Tagami, Properties of Injectable Apatite-Forming Premixed Cements, J. Res. Natl. Inst. Stand. Technol. 115 (2010) 233-241.

[33] S. A. Park, S. H. Lee, W. D. Kim, Fabrication of porous polycaprolactone/hydroxyapatite (PCL/HA) blend scaffolds using a 3D plotting system for bone tissue engineering, Bioprocess Biosyst. Eng. 34 (2011) 505-513. https://doi.org/10.1007/s00449-010-0499-2.

[34] S. Zhou, Y. B. Li, Y. Y. Wang, Y. Zuo, S. B. Gao, M. Li, L. Zhang, The porous structure and mechanical properties of injection molded HA/PA66 scaffolds, Int. Polym. Process. 29 (2014) 454-460. https://doi.org/10.3139/217.2851.

[35] K. K. Moncal, D. N. Heo, K. P. Godzik, D. M. Sosnoski, O. D. Mrowczynski, E. Rizk, V. Ozbolat, S. M. Tucker, E. M. Gerhard, M. Dey, G. S. Lewis, J. Yang, I. T. Ozbolat, 3D printing of poly(ε-caprolactone)/poly(D,L-lactide-co-glycolide)/hydroxyapatite composite constructs for bone tissue engineering, J. Mater. Res. 33 (2018) 1972-1986. https://doi.org/10.1557/jmr.2018.111.

[36] A. Alghunaim, S. Kirdponpattara, B. M. Z. Newby, Techniques for determining contact angle and wettability of powders, Powder Technol. 287 (2016) 201-215. https://doi.org/10.1016/j.powtec.2015.10.002.

[37] S. Mirzababaei, S. Pasebani, A Review on Binder Jet Additive Manufacturing of 316L Stainless Steel, J. Manuf. Mater. Process. 3 (2019) 82. https://doi.org/10.3390/jmmp3030082.

[38] S. H. Jariwala, G. S. Lewis, Z. J. Bushman, J. H. Adair, H. J. Donahue, 3D Printing of Personalized Artificial Bone Scaffolds, 3D Print. Addit. Manuf. 2 (2015) 56-64. https://doi.org/10.1089/3dp.2015.0001.

[39] R. Detsch, S. Schaefer, U. Deisinger, G. Ziegler, H. Seitz, B. Leukers, In vitro—Osteoclastic Activity Studies on Surfaces of 3D Printed Calcium Phosphate Scaffolds, J. Biomater. Appl. 26(2011) 359-380. https://doi.org/10.1177/0885328210373285.

[40] Z. Wang, A. A. Volinsky, N. D. Gallant, Nanoindentation study of polydimethylsiloxane elastic modulus using berkovich and flat punch tips, J. Appl. Polym. Sci. 132 (2015) 1-7. https://doi.org/10.1002/app.41384.

[41] J. W. Kim, K. H. Shin, Y. H. Koh, M. J. Hah, J. Moon, H. E. Kim, Production of poly(ε-caprolactone)/hydroxyapatite composite scaffolds with a tailored macro/microporous structure, high mechanical properties, and excellent bioactivity, Materials (Basel). 10 (2017). https://doi.org/10.3390/ma10101123.

[42] Y. Wang, Y. Xue, J. Wang, Y. Zhu, Y. Zhu, X. Zhang, J. Liao, X. Li, X. Wu, Y. X. Qin, W. Chen, A composite hydrogel with high mechanical strength, fluorescence, and degradable behavior for bone tissueengineering, Polymers (Basel). 11 (2019). https://doi.org/10.3390/polym11071112.

[43] M. Alizadeh-Osgouei, Y. Li, C. Wen, A comprehensive review of biodegradable synthetic polymer-ceramic composites and their manufacture for biomedical applications, Bioact. Mater. 4 (2019) 22-36. https://doi.org/10.1016/j.bioactmat.2018.11.003.

[44] A .R. Akkineni, Y. Luo, M. Schumacher, B. Nies, A. Lode, M. Gelinsky, 3D plotting of growth factor loaded calcium phosphate cement scaffolds. Acta Biomater. 27 (2015) 264-274. https://doi.org/10.1016/j.actbio.2015.08.036.

[45] H. S. Sohn, J. K. Oh, Review of bone graft and bone substitutes with an emphasis on fracture surgeries, Biomater. Res. 23 (2019) 4-10. https://doi.org/10.1186/s40824-019-0157-y.

[46] H. H. K. Xu, P. Wang, L. Wang, C. Bao, Q. Chen, M. D. Weir, L. C. Chow, L. Zhao, X. Zhou, M. A. Reynolds, Calcium phosphate cements for bone engineering and their biological properties, Bone Res. 5 (2017) 17056. https://doi.org/10.1038/boneres.2017.56.

[47] L. C. Chow. Next generation calcium phosphate-based biomaterials., Dent. Mater. J. 28 (2009) 1-10. https://doi.org/10.4012/dmj.28.1.

[48] J. Jančář, A. Sloviková, E. Amler, P. Krupa, H. Kecová, L. Plánka, P. Gal, A. Nečas. Mechanical response of porous scaffolds for cartilage engineering, Physiol. Res. 56 (2007).

[49] P. S. P. Poh, D. Valainis, K. Bhattacharya, M van Griensven, P. Dondl, Optimization of Bone Scaffold Porosity Distributions, Sci. Rep. 9 (2019) 1-10. https://doi.org/10.1038/s41598-019-44872-2.

[50] É. Lakatos, L. Magyar, I Bojtár, Material properties of the mandibular trabecular bone, J. Med. Eng. 2014 (2014). https://doi.org/10.1155/2014/470539.

[51] R. Y. Roca, A. Peura, M. P. Kowaleski, M. T. Watson, M. Lendhey, P. J. Rocheleau, D.A. Hulse, Ex vivo mechanical properties of a 2.5-mm bone anchor for treatment of cranial cruciate ligament rupture in toy breed dogs, Vet. Surg. (2020) 1-5. https://doi.org/10.1111/vsu.13399.

[52] J. A. Motherway, P. Verschueren, G. Van der Perre, J. Vander Sloten, M. D. Gilchrist, The mechanical properties of cranial bone: The effect of loading rate and cranial sampling position, J. Biomech. 42 (2009) 2129-2135. https://doi.org/10.1016/j.jbiomech.2009.05.030.

[53] T. J. Kriewall, Structural, mechanical, and material properties of fetal cranial bone, Am. J. Obstet. Gynecol. 143 (1982) 707-714. https://doi.org/10.1016/0002-9378(82)90119-3.

[54] J. H. McElhaney, J. L. Fogle, J. W. Melvin, R. R. Haynes, V. L. Roberts, N. M. Alem, Mechanical properties of cranial bone, J. Biomech. 3 (1970) 495-511. https://doi.org/10.1016/0021-9290(70)90059-X.

[55] E. F. Morgan, G. U. Unnikrisnan, A. I. Hussein, Bone Mechanical Properties in Healthy and Diseased States, Annu. Rev. Biomed. Eng. 20 (2018) 119-143. https://doi.org/10.1146/annurev-bioeng-062117-121139.

We claim:

1. A precursor composition comprising a non-aqueous slurry comprising a mixture of:
   a solid phase comprising a mixture of tetracalcium phosphate (TTCP) and dicalcium phosphate anhydrous (DCPA), and
   a non-aqueous liquid phase comprising a polymer and a non-aqueous solvent in which the polymer is soluble, wherein
      i) the non-aqueous solvent is selected from the group consisting of ethanol and tetrahydrofuran,
      ii) optionally the liquid phase further comprises at least one additional non-aqueous solvent selected from the group consisting of acetic acid, acetone, methanol, 2-propanol, butanol, 2-butoxyethanol, benzyl alcohol, 1-methoxy-2-propanol, butyl glycol, n-butyl acetate, N,N-dimethylacetamide, N,N-dimethylformamide, dimethylsulfoxide, N-methyl-2-pyrrolidone (NMP), carbon tetrachloride, benzene, toluene, cyclohexanone, 2-nitropropane, 2-butanone, acetonitrile, dichloromethane, chloroform, and ethyl acetate, and iii) the polymer is selected from the group consisting of poly(ethylene glycol), polyvinyl pyrrolidone (PVP), poly(methyl methacrylate) (PMMA), polyoxazoline, polyphosphoesters (PPE), dextran, polyvinyl butyral (PVB), polycaprolactone (PCL), and poly lactic-co-glycolic acid (PLGA).

2. The precursor composition of claim 1, wherein the TTCP has a particle size of 1 to 17 μm and the DCPA has a particle size of 1 to 5 μm.

3. The precursor composition of claim 1, wherein the TTCP and the DCPA are in a TTCP:DCPA weight ratio of about 73%:27% to about 20%:80%, and wherein the solid:liquid phases are in a weight ratio of 0.1:1 to 2:1.

4. The precursor composition of claim 1, wherein the solid phase has a Ca/P molar ratio of 1.33 to 1.9.

5. The precursor combination of claim 1, wherein the solid phase further comprises at least one of α-TCP and β-TCP, ACP, OCP, DCPD, MCPM, MCPA, $CaCO_3$, CaO and $Ca(OH)_2$.

6. The precursor composition of claim 1, further comprising a hardening accelerator.

7. The precursor composition of claim 6, wherein the hardening accelerator is at least one selected from the group consisting of sodium phosphate dibasic, monosodium phosphate, trisodium phosphate, ammonium phosphate, ammonium dihydrogen phosphate, monopotassium phosphate, dipotassium phosphate, tripotassium phosphate, sodium fluoride, potassium fluoride, sodium acetate, potassium oxalate, sodium sulfate, sodium cacodylate, glycolic acid, citric acid, tartaric acid, malonic acid, malic acid, and maleic acid.

* * * * *

UNITED STATES PATENT AND TRADEMARK OFFICE
CERTIFICATE OF CORRECTION

| | | |
|---|---|---|
| PATENT NO. | : 11,684,699 B2 | Page 1 of 1 |
| APPLICATION NO. | : 16/894128 | |
| DATED | : June 27, 2023 | |
| INVENTOR(S) | : Alimperti et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 329 days.

Signed and Sealed this
Twelfth Day of November, 2024

Katherine Kelly Vidal
*Director of the United States Patent and Trademark Office*